US010189052B2

(12) United States Patent
Rubel et al.

(10) Patent No.: US 10,189,052 B2
(45) Date of Patent: Jan. 29, 2019

(54) METHODS OF DRIVING POLARIZATION INVERSION IN FERROELECTRIC MATERIALS AND DEVICES

(71) Applicant: THUNDER BAY REGIONAL RESEARCH INSTITUTE, Thunder Bay (CA)

(72) Inventors: Oleg Rubel, Ancaster (CA); Samuel Pichardo, Thunder Bay (CA); Laura Curiel, Thunder Bay (CA); Sheikh Jamil Ahmed, Hamilton (CA); Jeremy Cole, Rainy River (CA)

(73) Assignee: THUNDER BAY REGIONAL HEALTH RESEARCH INSTITUTE, Thunder Bay, ON (CA)

( * ) Notice: Subject to any disclaimer, the term of this patent is extended or adjusted under 35 U.S.C. 154(b) by 433 days.

(21) Appl. No.: 15/037,719

(22) PCT Filed: Nov. 21, 2014

(86) PCT No.: PCT/CA2014/051113
§ 371 (c)(1),
(2) Date: May 19, 2016

(87) PCT Pub. No.: WO2015/074153
PCT Pub. Date: May 28, 2015

(65) Prior Publication Data
US 2016/0288166 A1 Oct. 6, 2016

Related U.S. Application Data

(60) Provisional application No. 61/907,046, filed on Nov. 21, 2013.

(51) Int. Cl.
H01L 41/22 (2013.01)
B06B 1/06 (2006.01)
(Continued)

(52) U.S. Cl.
CPC .................. *B06B 1/06* (2013.01); *A61N 7/00* (2013.01); *B06B 1/0207* (2013.01);
(Continued)

(58) Field of Classification Search
CPC ....... B06B 1/06; B06B 1/0207; B06B 1/0215; B06B 1/0238; A61N 7/00; H01L 41/042; H01L 41/047; H01L 41/09
(Continued)

(56) References Cited

U.S. PATENT DOCUMENTS 2,944,117 A 7/1960 Gray
4,729,620 A 3/1988 Paviath
(Continued)

FOREIGN PATENT DOCUMENTS

EP 0915524 12/1999
JP 2002280631 9/2002
RU 2288785 12/2009

OTHER PUBLICATIONS

S. Barsukov et al., J. Advan. Res. Phys. 2, 1-4 2011.
(Continued)

Primary Examiner — Thomas Dougherty
(74) Attorney, Agent, or Firm — Hill & Schumacher

(57) ABSTRACT

Methods and devices are described for driving ferroelectric perovskite oxide crystals to achieve polarization inversion with reduced coercivity. In some embodiments, the anisotropy in the potential energy surface of a ferroelectric material is employed to drive polarization inversion and switching with a reduced coercive field relative to uniaxial excitation. In some embodiments, polarization inversion with reduced coercivity is produced via the application of an electric field that exhibits a time-dependent orientation, in contrast with conventional uniaxial electrical excitation, thereby causing the central ion (and the crystal structure as (Continued)

a whole) to evolve along a lower-energy path, in which the central ion is driven such that it avoids the potential energy maximum. This may be achieved, for example, by applying at least two non-parallel time-dependent voltages (e.g. bias, potential) such that orientation of the electric field changes with time during the switching cycle.

20 Claims, 22 Drawing Sheets

(51) Int. Cl.
| | |
|---|---|
| A61N 7/00 | (2006.01) |
| B06B 1/02 | (2006.01) |
| H01L 41/04 | (2006.01) |
| H01L 41/047 | (2006.01) |
| H01L 41/09 | (2006.01) |
| B08B 3/12 | (2006.01) |
| A61B 8/12 | (2006.01) |
| A61B 8/00 | (2006.01) |

(52) U.S. Cl.
CPC .......... *B06B 1/0215* (2013.01); *B06B 1/0238* (2013.01); *H01L 41/042* (2013.01); *H01L 41/047* (2013.01); *H01L 41/09* (2013.01); *A61B 8/12* (2013.01); *A61B 8/4483* (2013.01); *A61B 8/546* (2013.01); *A61N 2007/0043* (2013.01); *B06B 2201/71* (2013.01); *B06B 2201/72* (2013.01); *B06B 2201/76* (2013.01); *B08B 3/12* (2013.01)

(58) Field of Classification Search
USPC .......................... 310/357–359; 264/435, 436
See application file for complete search history.

(56) References Cited

U.S. PATENT DOCUMENTS

| | | | | |
|---|---|---|---|---|
| 5,056,366 | A | | 10/1991 | Fersht et al. |
| 5,111,320 | A | | 5/1992 | Wysocki et al. |
| 5,555,219 | A | * | 9/1996 | Akiyama ................ C04B 35/26 |
| | | | | 252/299.01 |
| 8,604,676 | B1 | * | 12/2013 | Finkel ................... H01L 41/187 |
| | | | | 310/358 |
| 2009/0021111 | A1 | | 1/2009 | Ue |
| 2010/0073823 | A1 | | 3/2010 | Aoki et al. |

OTHER PUBLICATIONS

Fu, H. et al., Nature 403, 281-283, 2000.
Khakhomov, S. A. et al, J. Auto, Mob. Rob. and Intell. Sys, 199-201, 2009.
Huber, J.E. et al., "Multi-axial electrical switching of a ferroelectric; theory versus experiment", Journal of the Mechanics and Physics of Solids, pp. 785-811, department of Engineering, University of Cambridge, 2001.
Cole, J. et al., "Marble game with optimal ferroelectric switching", J Phys condens Matter, Thunder Bay Regional Institute et al.: Thunder Bay, Ontario, Canada. Apr. 2, 2014 Abstract.
J. J. Hong and D. Vanderbilt (2011), "Mapping the energy surface of PbTiO3 in multidimensional electric-displacement space", Physical Review B 84:115107-1-115107-6.
S.J. Ahmed, J. Kivinen, B. Zaporzan, L. Curiel, S. Pichardo, and O. Rubel (2013), "BerryPI: A software for studying polarization of crystalline solids with WIEN2k density functional all-electron package", Computer Phys. Comms. 184:647-651.
International Search Report—PCT/CA2014/051113 dated Apr. 10, 2015.
PCT Written Opinion—PCT/CA2014/051113 dated Apr. 10, 2015.

* cited by examiner

| Structural parameters | Tetragonal ($T_1$) | Tetragonal ($T_2$) | Cubic (C) |
|---|---|---|---|
| $a, b, c$ (Å) | (3.86, 3.86, 4.04) | (4.04, 3.86, 3.86) | (3.92, 3.92, 3.92) |
| $u_{Ti}$ | (0.5, 0.5, 0.5328) | (0.5328, 0.5, 0.5) | (0.5, 0.5, 0.5) |
| $u_{O_1}$ | (0.5, 0.5, 0.0902) | (0.6023, 0.5, 0) | (0.5, 0.5, 0) |
| $u_{O_2}$ | (0.5, 0, 0.6023) | (0.6023, 0, 0.5) | (0.5, 0, 0.5) |
| $u_{O_3}$ | (0, 0.5, 0.6023) | (0.0902, 0.5, 0.5) | (0, 0.5, 0.5) |

| Tx number | mode | Impedance before matching ($\Omega$) | Impedance after matching ($\Omega$) | Resonant frequency (kHz) |
|---|---|---|---|---|
| 1 | P | $225 - j174$ | $50 - j1$ | 453.8 |
|   | L | $136 - j45$ | $49 - j1$ | 447 |
| 2 | P | $250 - j270$ | $49 - j2$ | 463.7 |
|   | L | $127 - j44$ | $50 - j0.3$ | 464.35 |
| 3 | P | $226 - j158$ | $48 - j1$ | 465.65 |
|   | L | $104 - j42$ | $49 - j0.1$ | 467.8 |
| 4 | P | $290 - j230$ | $49 - j1.6$ | 466 |
|   | L | $117 - j56$ | $50 - j1$ | 463.15 |

FIG. 20

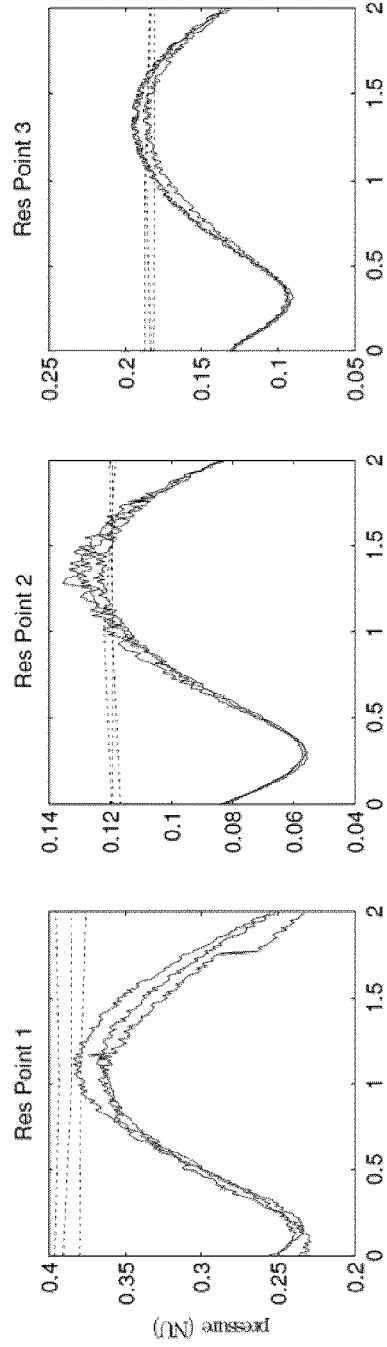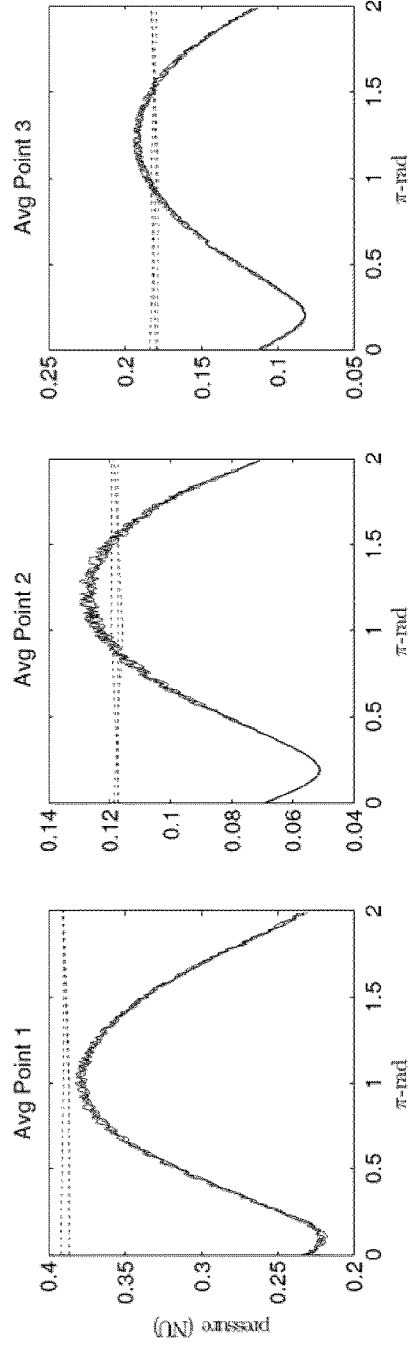
FIG. 21A  FIG. 21B  FIG. 21C  FIG. 21D  FIG. 21E  FIG. 21F

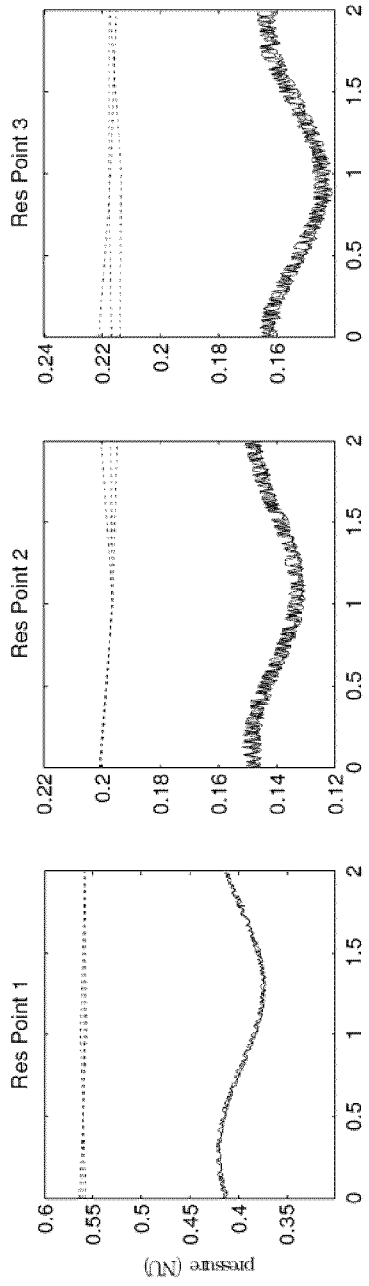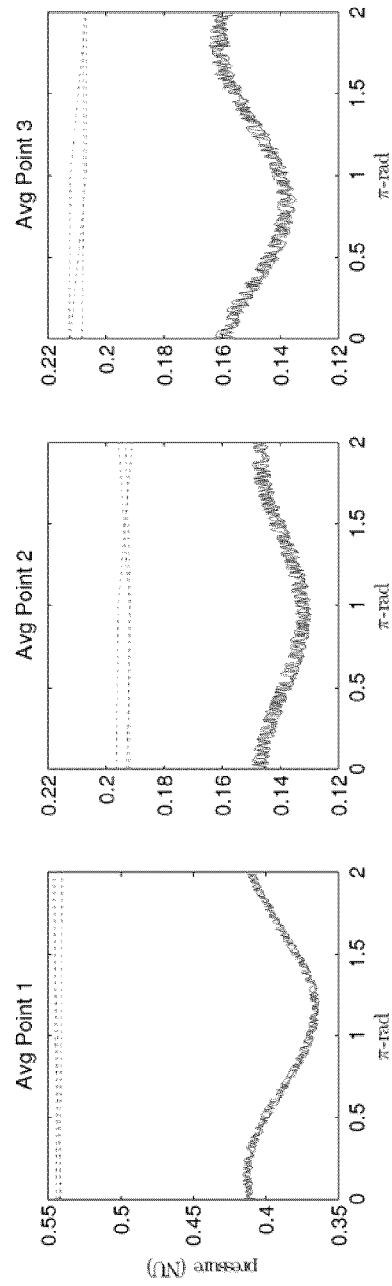
FIG. 22A  FIG. 22B  FIG. 22C  FIG. 22D  FIG. 22E  FIG. 22F

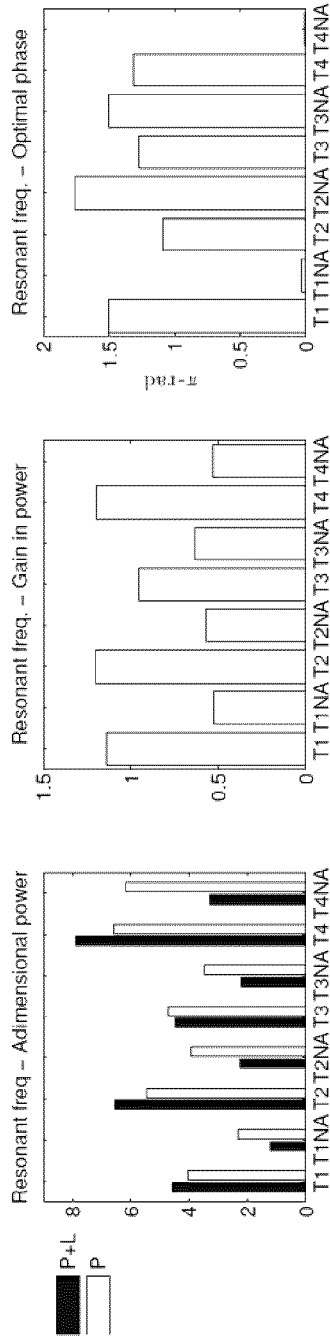
FIG. 24A
FIG. 24B
FIG. 24C
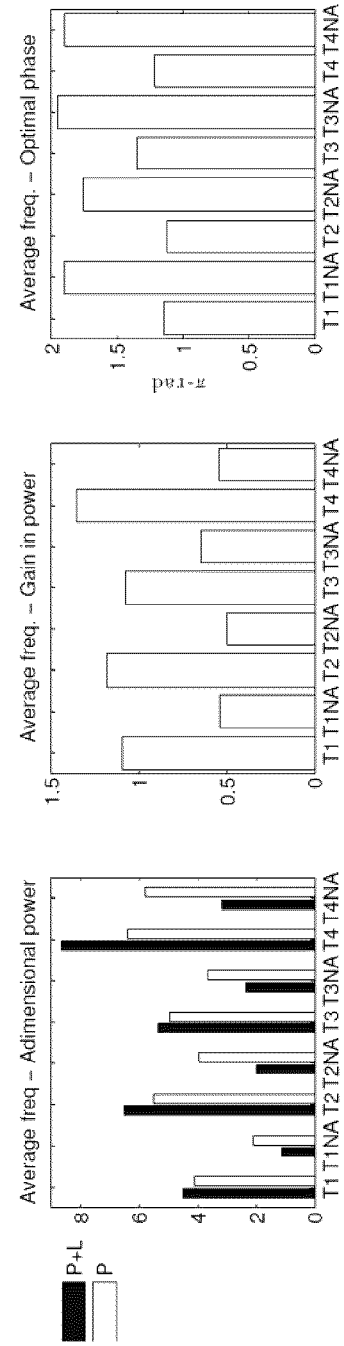
FIG. 24D
FIG. 24E
FIG. 24F

US 10,189,052 B2

METHODS OF DRIVING POLARIZATION INVERSION IN FERROELECTRIC MATERIALS AND DEVICES

CROSS-REFERENCE TO RELATED APPLICATION

This application is a National Phase application claiming the benefit of the international PCT Patent Application No. PCT/CA2014/051113, filed on Nov. 21, 2014, in English, which claims priority to U.S. Provisional Application No. 61/907,046, titled "METHODS OF DRIVING POLARIZATION INVERSION IN FERROELECTRIC MATERIALS AND DEVICES" and filed on Nov. 21, 2013, the entire contents of which are incorporated herein by reference.

BACKGROUND

The present disclosure relates to ferroelectric materials and devices. In particular, the present disclosure relates to methods of electrically driving ferroelectric devices and elements.

Some ferroelectric materials exist as perovskite metal-oxide compound ceramics with a general chemical formula $ABO_3$, where A and B are different cations. These materials crystallize in a cubic structure shown in FIG. 1A above their Curie Temperature. As shown in FIG. 1A, the 'A' atom sits at cube corner positions (0, 0, 0), type 'B' atom sits at body centre position (½, ½, ½) and oxygen atoms sit at face-centered positions (½, ½, 0).

As noted above, such centrosymmetric (cubic) structures exist only at high temperatures (above Curie temperature). At temperatures below the Curie temperature, the structure transforms into a tetragonal form, as shown in FIG. 1B. The distinct feature of the tetragonal structure is the presence of a non-zero polarization due to a shift of atom "B" from its centrosymmetric position.

The tetragonal phase also exhibits pyroelectric and ferroelectric properties, such that the crystal domains possess a spontaneous polarization in the absence of an external electric field. In ferroelectrics, the polarization direction can be reversed under the application of a sufficiently large external electric field. Such piezoelectric crystals change their macroscopic dimensions in response to an external electric field. This is the property that is utilized in ultrasound transducers and generators, and other devices. In particular, lead-based perovskites $PbZr_xTi_{1-x}O_3$ (PZT) have emerged as one of the most widely studied and technologically important class of ferroelectric oxides. This alloy exhibits an enhancement of electromechanical response near to the morphotropic phase boundary (MPB) at $x \approx 0.4$-$0.5$ that exceeds by far the properties of individual constituents $PbZrO_3$ and $PbTiO_3$. The enhancement of the piezoelectric response near MPB is attributed to "flattening" of an energy surface that facilitates inversion of the spontaneous polarization [1-4].

FIG. 2A shows a typical piezoelectric element 100, consisting of a ferroelectric piezoelectric material sandwiched between two contacts 105 and 110, as shown in FIGS. 2A and 2B. When an alternating potential is applied to the contacts, the crystal undergoes expansion/contraction cycles, due to the electric field 120.

During the cycle, the central atom switches its position, as shown in FIG. 3, which results in a polarization inversion [1]. For the switching process to occur, the electric field (or bias voltage) must exceed its critical (coercive) magnitude, which is a material-specific property. The coercive field $E_c$, is the electric field at which the polarization inversion occurs, as shown in the figure.

The notable feature of the polarization vs. applied electric field (or bias voltage) plot is the existence of a hysteresis loop (see FIG. 3). The area of this loop determines parasitic losses in the ferroelectric crystal, which are responsible for incomplete conversion of the electrical power into useful mechanical signal. The unused electrical energy can partly transform into the heat, similar to the dielectric heating in a microwave oven. Heating of the piezoelectric element is an unwanted effect, and requires special care for its dissipation [2]. In practical applications, this limits the functionality of certain devices by causing the element to overheat. Therefore, a reduction of the coercive electric field (or bias voltage) is important for improvement in the efficiency of piezoelectric actuators and reduction of the electrical power required to drive the transducer.

SUMMARY

Methods and devices are described for driving ferroelectric perovskite oxide crystals to achieve polarization inversion with reduced coercivity. In some embodiments, the anisotropy in the potential energy surface of a ferroelectric material is employed to drive polarization inversion and switching with a reduced coercive field relative to uniaxial excitation. In some embodiments, polarization inversion with reduced coercivity is produced via the application of an electric field that exhibits a time-dependent orientation, in contrast with conventional uniaxial electrical excitation, thereby causing the central ion (and the crystal structure as a whole) to evolve along a lower-energy path, in which the central ion is driven such that it avoids the potential energy maximum. This may be achieved, for example, by applying at least two non-parallel time-dependent voltages (e.g. bias, potential) such that orientation of the electric field changes with time during the switching cycle.

Accordingly, in one aspect, there is provided a method of electrically driving a ferroelectric material to achieve polarization inversion, the ferroelectric material having an anisotropic potential energy surface with an energy barrier for a curved switching path that is lower than for the barrier for a direct path associated with uniaxial switching, the method comprising:

applying time-dependent voltages to the ferroelectric material in at least two directions; and controlling the voltages such that the orientation of the electric field within the ferroelectric material varies with time during the switching cycle, and such that the coercive field is reduced relative to the coercive field required for uniaxial excitation;

wherein the voltages are applied such that the coercive field is exceeded during the switching cycle, thereby achieving polarization inversion.

In another aspect, there is provided a method of electrically driving an ultrasonic device, the ultrasonic device comprising one or more ferroelectric elements having an anisotropic potential energy surface with an energy barrier for a curved switching path that is lower than for the barrier for a direct path associated with uniaxial switching, the method comprising:

applying time-dependent voltages to the one or more ferroelectric elements in at least two directions; and controlling the voltages such that the orientation of the electric field within the one or more ferroelectric elements varies with time during the switching cycle, and such that the coercive field is reduced relative to the coercive field required for uniaxial excitation;

wherein the voltages are applied such that the coercive field is exceeded during the switching cycle, thereby achieving polarization inversion.

In another aspect, there is provided an ultrasonic device comprising:

one or more ferroelectric elements, each ferroelectric element having an anisotropic potential energy surface with an energy barrier for a curved switching path that is lower than for the barrier for a direct path associated with uniaxial switching; and control circuitry connected to the ferroelectric elements for applying time-dependent voltages to the one or more ferroelectric elements in at least two directions;

wherein the voltages are provided by the control circuitry such that the orientation of the electric field within the one or more ferroelectric elements varies with time during the switching cycle, and such that the coercive field is reduced relative to the coercive field required for uniaxial excitation; and wherein the voltages are provided by the control circuitry such that the coercive field is exceeded during the switching cycle, thereby achieving polarization inversion.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 7A shows the electrode configuration and the resulting rotating internal electric field, while FIG. 7B shows the phase delay between the two applied voltages.

FIG. 9 is a table listing structural parameters (fractional coordinates u and lattice constants a, b and c) for $PbTiO_3$ in two distinct phases obtained from self-consistent density functional theory (DFT) calculations. The position of Pb-atom is assumed to be fixed at the origin (0,0,0).

FIG. 18A shows the cross-section view of mounting of the ring transducer, where an absorber is placed at center of opening. FIG. 18B shows a top view of the ring transducer and absorber. FIG. 18C shows the connection of "lateral" (L) mode electrodes where the power supply drives the inner and outer faces of the ring, while FIG. 18D shows the connection of "propagation" (P) mode electrodes where the power supply drives the top and bottom faces of the ring.

FIG. 20 is a table showing the electrical characterization of the transducers.

FIGS. 21A-F plot the RMS value of pressure P+L in non-dimensional units (NU) vs. phase in L mode for each of 3 points measured for transducer #4. Solid lines show the measurements for the P+L configuration. Dashed lines show the measurements for the P mode. Top row shows measurements using each resonant frequency in each of P and L modes. Bottom row shows measurements using the average frequency of both modes. Measurements were done with the absorber in place.

FIGS. 22A-F plot the RMS value of pressure P+L in non-dimensional units (NU) vs. phase in L mode for each of 3 points measured for transducer #4. Solid lines show the measurements for the P+L configuration. Dashed lines show the measurements for the P mode. Top row shows measurements using each resonant frequency in each of P and L modes. Bottom row shows measurements using the average frequency of both modes. Measurements were done without the absorber in place.

FIG. 23A shows measurement from the P+L configuration with absorber. FIG. 23B shows measurement from the P mode with absorber. FIG. 23C shows measurement from the P+L configuration without absorber. FIG. 23D shows measurement from the P configuration without absorber.

FIGS. 24A-F plot the consolidated results of gain in efficiency and optimal phase. Data compares each transducer with and without the absorber in place. Labels indicating data without the absorber have the suffix "NA". On left column, the non-dimensional power for each transducer is shown for the P+L and P configurations. On the central column, the gain of the power of the P+L combination over the P mode is shown. On the right column, the optimal phase to drive the L mode in the P+L configuration is detailed. The top row shows the data when driving the each mode of the transducer at its resonant frequency and the bottom row when driving to the average frequency of both modes.

DETAILED DESCRIPTION

Figure 1A:
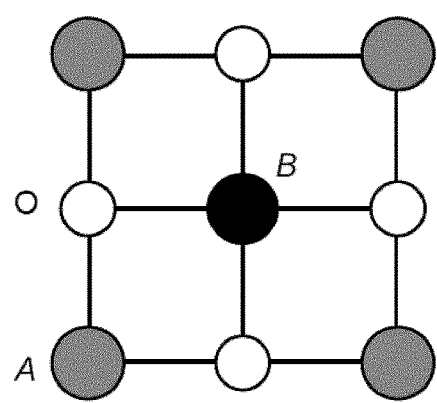
FIGS. 1A and 1B show different phases of a perovskite ferroelectric crystal, including the (A) cubic and (B) tetragonal phases.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "ferroelectric perovskite oxide" refers to a ferroelectric material having a chemical formula $ABO_3$ and having a pyroelectric and piezoelectric phase below a Curie temperature. Examples of ferroelectric perovskite oxides include $PbTiO_3$, $BaTiO_3$, and $LiNbO_3$. In some embodiments, a "ferroelectric perovskite oxide" may be an antiferroelectric perovskite oxide.

As used herein, the phrases "coercive field", "coercive electric field", and "coercivity" refer to the electric field required to induce polarization inversion. In some aspects, such as the mathematical modeling of polarization inversion in single crystals described below, the coercive field is the intrinsic coercive field. In other aspects, such as those pertaining to crystalline ferroelectric materials and devices exhibiting a domain structure (either as single or polycrystalline materials), the coercive field is the extrinsic coercive field.

Figure 3:
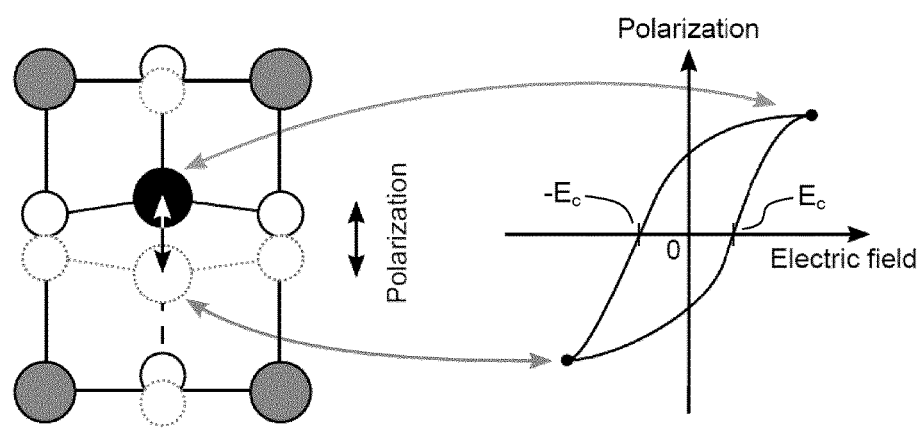
FIG. 3 illustrates the hysteresis in the relationship between the applied electric field, the resulting polarization and structural changes that accompany the polarization inversion.

As described below, various embodiments of the present disclosure provide devices and methods for producing polarization inversion in ferroelectric materials with reduced coercivity. It was previously believed that for ferroelectric perovskite oxide elements, the transition between two states with opposite polarization (see FIG. 3) occurs by moving the central atom along the straight line connecting its positions in the top and bottom configuration. This polarization inversion was thus originally viewed as a structural transformation with an intermediate transition via the centrosymmetric (cubic) structure with zero polarization.

Figure 4:
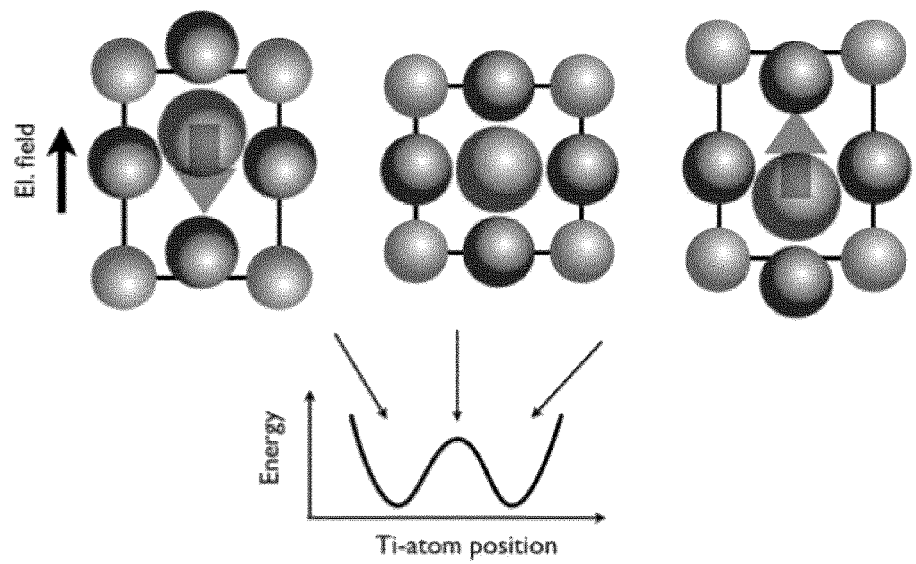
FIG. 4 is an illustration of the double-well potential energy profile associated with the motion of the central ion through a vertical line connecting the two orientations associated with the different polarization states of a ferroelectric perovskite material.

This transition typically features a double-well potential energy profile as shown in FIG. 4. This process corresponds to a 180° flip of polarization and requires overcoming of a large energy barrier (the particular magnitude of which is material-specific), since the centrosymmetric structure is unfavorable below the Curie temperature. The transformation between two structures manifests in the appearance of the hysteresis loop shown in FIG. 3.

Figure 5:
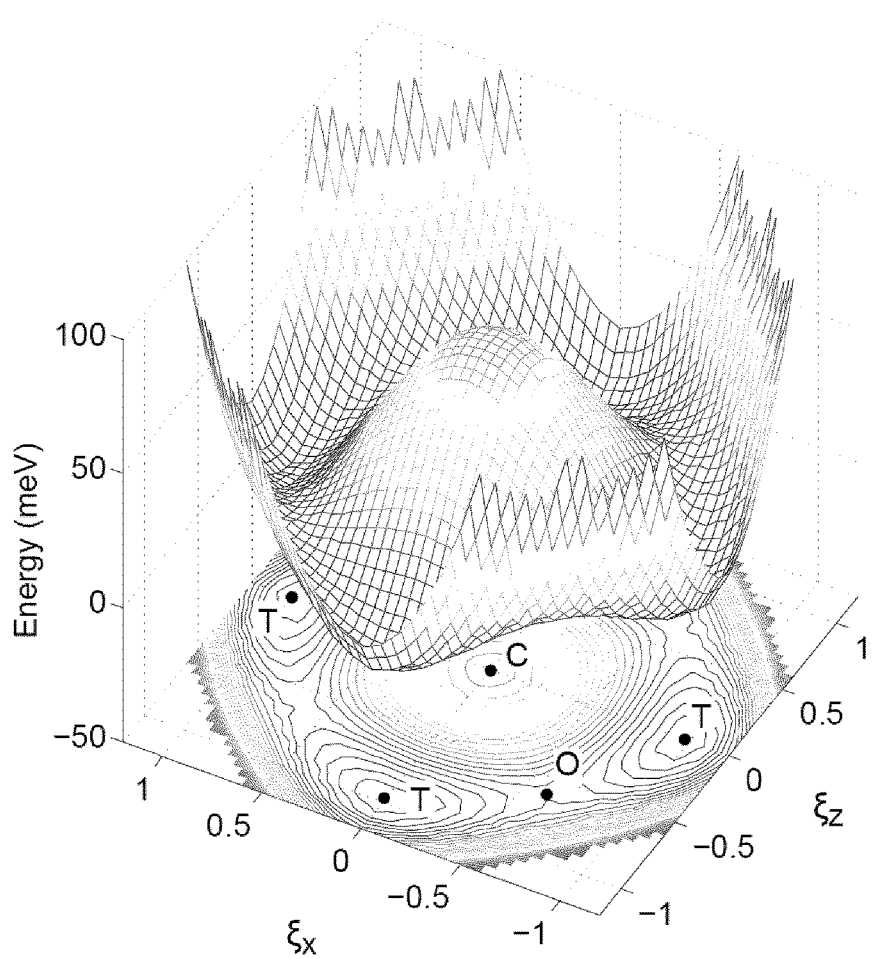
FIG. 5 is an illustration of the potential energy surface associated with the motion of the central ion within a planar surface passing through the center of the unit cells, showing the central maximal peak. The energy surface is calculated from first principles for the polarization inversion in (010) plane of $PbTiO_3$. The labels C, T and O refer to cubic, tetragonal and orthorhombic structures, respectively.

FIG. 5 illustrates the two-dimensional potential energy profile for a PbTiO$_3$ ceramic, which is the basis for PZT—one of the most technologically relevant piezoelectric materials (these results were obtained using Wien2k density functional software package [3] in conjunction with BerryPI package for polarization calculations [4]). On this plot, there are four local energy minima that correspond to the tetragonal structure marked as (T). The most unfavorable (high energy) transition state for switching is located at the center of the contour plot, which corresponds to the cubic structure (C-point). According to the previous conventional understanding of this phenomenon, the common approach for driving ferroelectric devices, such as ultrasound generators, forces the central atom to transition directly through the cubic structure and therefore through the highest energy, most unfavorable point.

Figure 6:
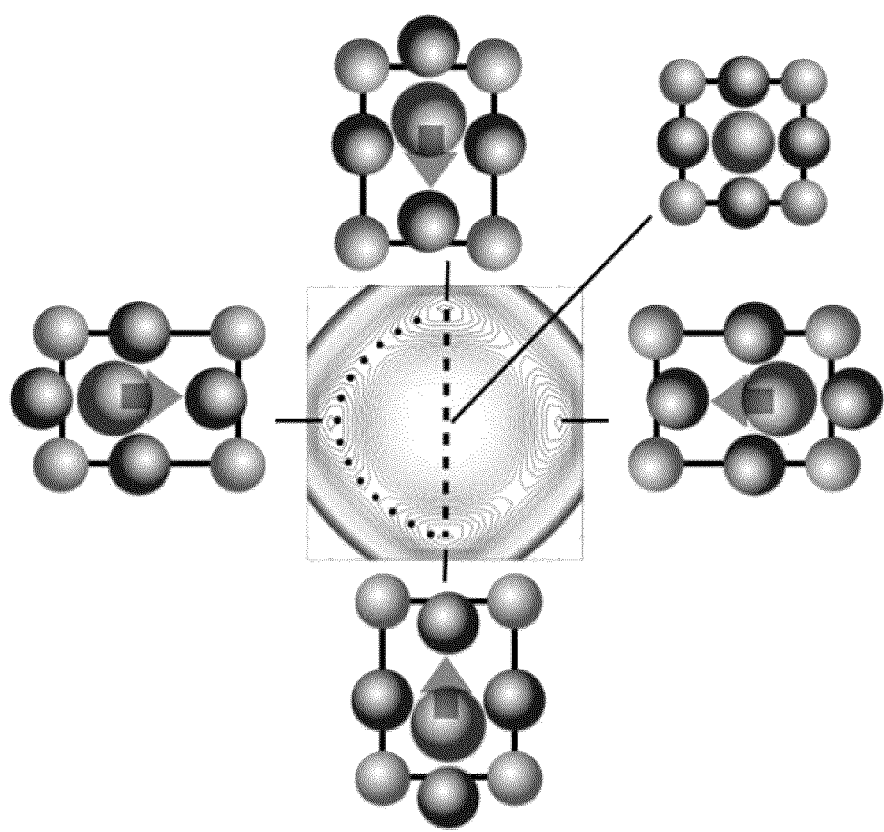
FIG. 6 shows a projection of the energy surface shown in FIG. 5, illustrating the position of the central ion at various locations on the energy surface.

The present inventors have recognized that the energy diagram shown above illustrates strong anisotropy in the coercive field, and that this anisotropy can be employed to produce polarization inversion with a reduced applied coercive voltage or bias. In particular, the aforementioned uniaxial method of driving the central ion through the central maxima of the anisotropic potential energy surface represents only one of a multitude of possible transition paths, and this path is not an energetically favorable path. This is clearly shown in FIG. 6, which shows both the uniaxial path (shown by the long-dashed line), and also an alternative, lower energy path (shown by the short-dashed line) that involves the application of a reduced coercive field (and associated applied bias).

Accordingly, in various embodiments described below, this anisotropy in the potential energy surface is employed to produce methods of driving (e.g. electrically exciting, generating, producing) polarization inversion (e.g. switching) in a ferroelectric material (e.g. crystal, device, or element) with a reduced coercive field relative to uniaxial excitation, where the ferroelectric material possess an anisotropic potential energy surface having an energy barrier for a curved switching path that is lower than for the barrier for a direct path associated with uniaxial switching. Examples of such ferroelectric materials are ferroelectric perovskite oxide crystals. As described in detail below, polarization inversion with reduced coercivity can be obtained via the application of an electric field that exhibits a time-dependent orientation, in contrast with conventional uniaxial electrical excitation, thereby causing the central ion (and the crystal structure as a whole) to evolve along a lower-energy path such as the path shown in FIG. 6, in which the central ion is driven such that it avoids the potential energy maximum.

Figure 7A:
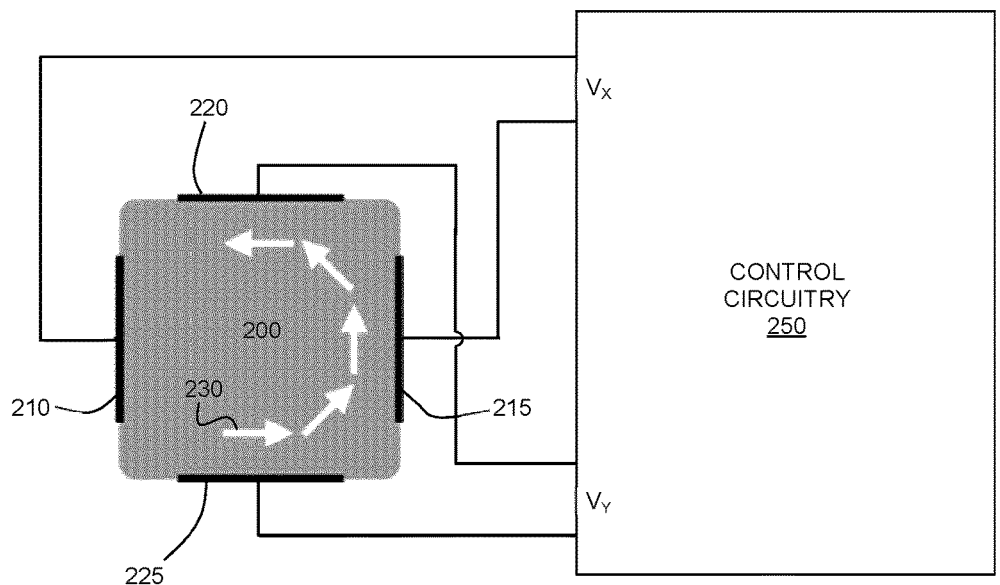
FIGS. 7A and 7B illustrate an example method of driving a ferroelectric element with a phase delay between two orthogonally applied voltages, in order to generate a rotating electric field within the element.
Figure 7B:
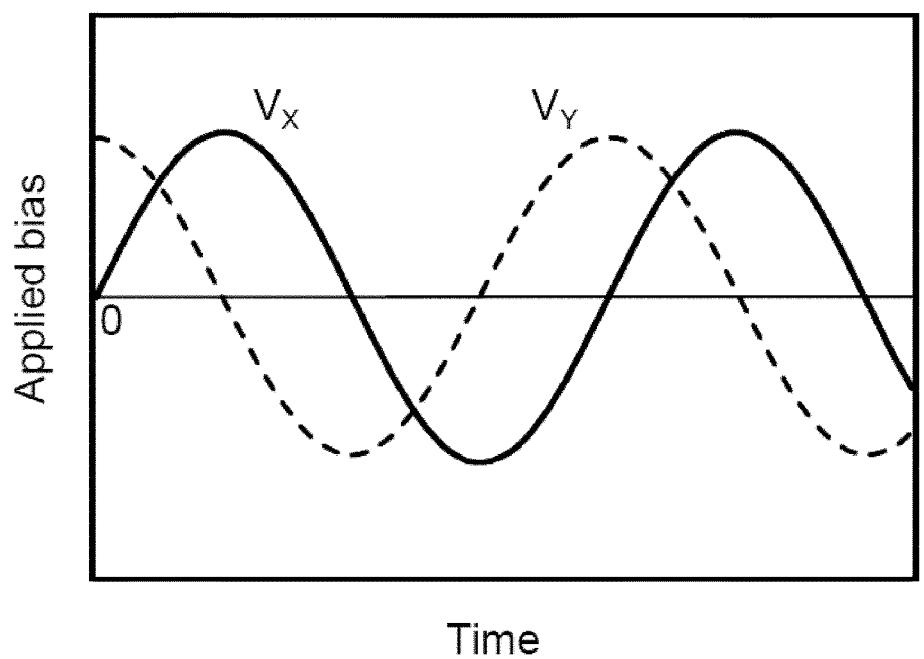

This may be achieved, for example, by applying at least two non-parallel time-dependent voltages (e.g. bias, potential) such that the direction of the electric field changes with during the switching cycle. One example implementation for achieving such a time-dependent reorientation of the electric field during a switching cycle is illustrated in FIGS. 7A and 7B. FIG. 7A shows ferroelectric element consisting of the ferroelectric material 200 and two pairs of electrodes 205-220, where the pairs of electrodes are shown positioned orthogonally in this example implementation. Control circuitry 250 is employed to generate and provide output voltages $V_X$ and $V_Y$. FIG. 7B shows an example time-dependent voltage profile for the voltage sources, which produces a rotating electric field 230 within element 200. In one example implementation, control circuitry 250 may include one or more voltage sources and circuitry for establishing a relative amplitude, frequency, and phase delay between two or more sets of output voltages. In some embodiments, control circuitry 250 may include a processor and a memory for controlling the amplitude, phase and/or frequency of the voltage outputs. Alternatively, the phase relationship between the voltage sources may be established by an external trigger.

It is further noted that due to the reduced coercivity needed according the methods and devices disclosed herein, polarization inversion switching can be achieved with less energy dissipation that via traditional uniaxial excitation. This reduction in energy dissipation can be useful for devices and applications, such as, but not limited to, ferroelectric transducers and memory elements.

Aspects of the present disclosure are now described and explained with reference to the following mathematical model, in which embodiments involving polarization inversion via rotation of the polarization of single-domain ferroelectric perovskite oxide crystals is investigated. The model shows a strong anisotropy of the coercive field that which originates from a peculiar free-energy surface for polarization inversion for the crystal. It is to be understood that this model is provided for heuristic purposes and is not intended to limit the scope of the disclosure to single crystal devices and applications, and that other ferroelectric materials other than ferroelectric perovskite crystals may be employed, provided that the ferroelectric material possess a potential energy surface having an energy barrier for a curved switching path that is lower than for the barrier for a direct path associated with uniaxial switching. Examples of other types of ferroelectric materials include order-disorder ferroelectric materials such as NaNO$_2$.

This example is structured as follows. First, structural transformations for the polarization inversion in PbTiO$_3$ are identified, associated energy surfaces are mapped (Sec. I). The results are used to justify Landau-Devonshire parametrization of the energy surface (Sec. II) that makes the present considerations more general. Next, the anisotropy of ferroelectric switching is investigated as a function of model parameters, which leads to determining suitable and/or optimal conditions for electrical excitations that result in reduced coercivity (Sec. III).

I. Mapping the Energy Surface

Figure 1B:
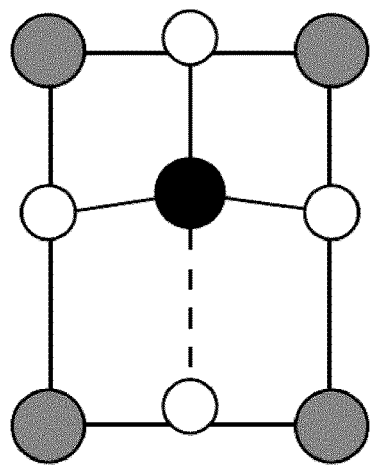
Figure 2A:
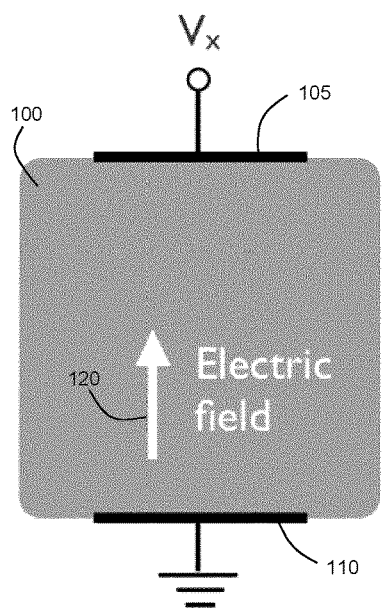
FIGS. 2A and 2B show the application of a time-varying electric field between parallel electrodes of a piezoelectric crystal, in order to obtain a mechanical response.
Figure 2B:
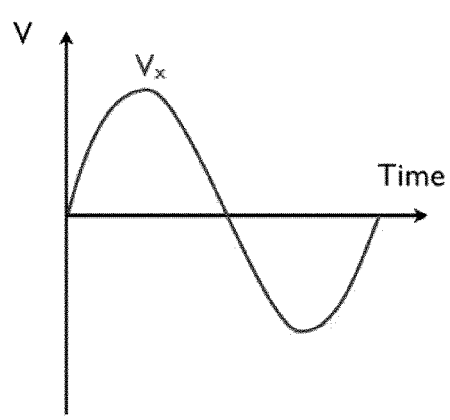
Figure 8:
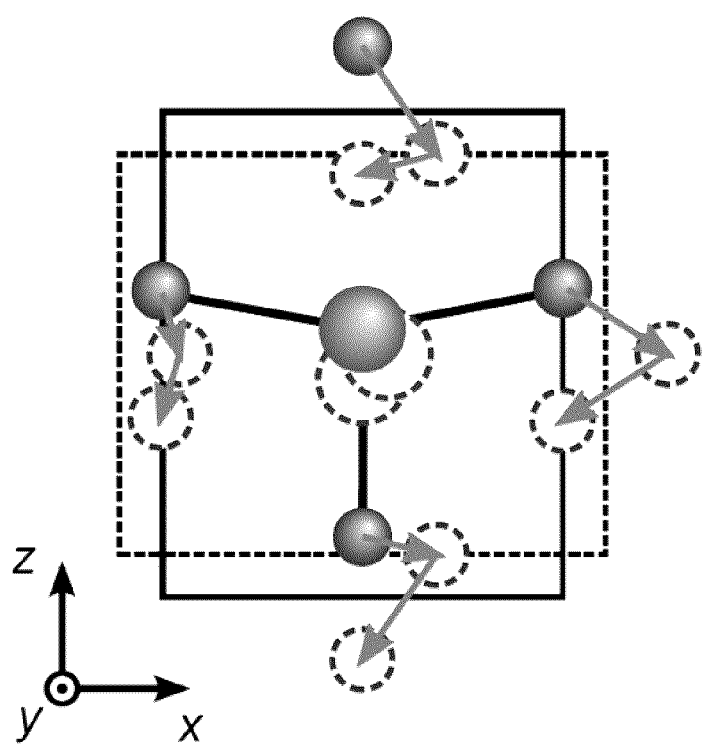
FIG. 8 illustrates the evolution of the tetragonal structure of $PbTiO_3$ in (010) Ti-centred plane during the ferroelectric switching by polarization rotation.

Below the Curie temperature, PbTiO$_3$ has a tetragonal structure, as shown in FIG. 1B, and as described above. The possible structural transformation corresponding to the polarization rotation in PbTiO$_3$ can involve an orthorhombic phase, which has the second lowest energy after the tetragonal one [6]. In this case, the polarization evolves in {010} plane following the structural transformations as illustrated in FIG. 8. The change in atomic positions is accompanied by changes of lattice parameters. Since the exact transition path is a priori unknown, the entire configurational space needs to be explored. With this purpose a two-dimensional configurational coordinate is introduced $\xi=(\xi_x, \xi_z)$, which represents an arbitrary transition structure. The equilibrium tetragonal structures with the spontaneous polarization pointing "up", "down", "left" and "right" are represented by $\xi=(0,+1)$, $(0,-1)$, $(-1,0)$ and $(+1,0)$, respectively; the centrosymmetric cubic structure corresponds to $\xi=(0,0)$. Atomic positions and lattice parameters (a and c) are then transformed according to:

$$u_{Ti}(\xi_x,\xi_z)=u_{Ti}^{(C)}+\xi_z(u_{Ti}^{(T_1)}-u_{Ti}^{(C)})+\xi_x(u_{Ti}^{(T_2)}-u_{Ti}^{(C)}). \quad (1)$$

Figure 10:
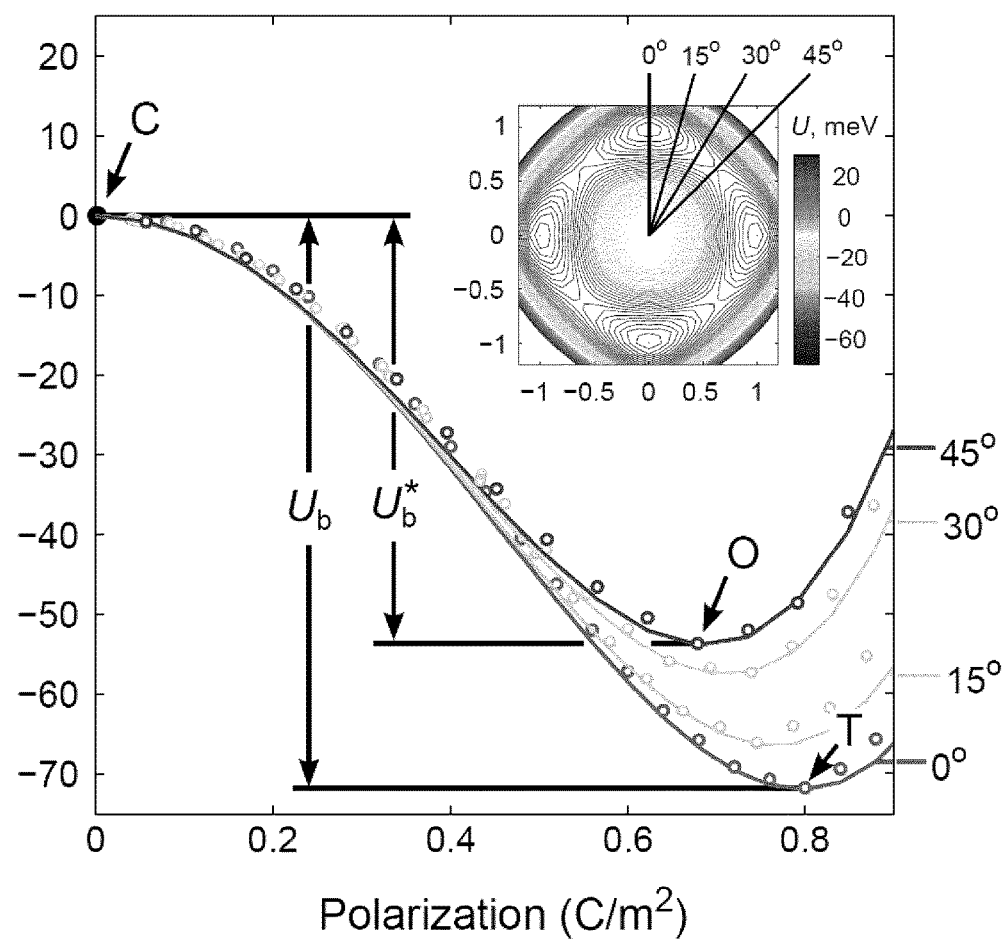
FIG. 10 plots the barrier heights $U_b$ and $U_b^*$ associated with transition between cubic (C), tetragonal (T) and orthorombic (O) structures. The inset shows energy surface as a function of polarization $\sqrt{(P_x^2+P_z^2)}$ sliced at different angles as shown in the inset. Solid lines represent fitting to Eq. (2) with parameters described in the specification.

Here (T$_1$), (T$_2$) and (C) refer to the equilibrium structural parameters corresponding to tetragonal ("up" and "right"

polarization) and cubic structures, respectively (see FIG. 10). The volume conservation is enforced when calculating the lattice parameter b.

A set of structures are then generated that map the configurational space within the range of $\xi_{x,y} \in [-1.2, +1.2]$ with the step size of $\Delta\xi=0.1$ and compute their Kohn-Sham total energies as described in the Example 1. The corresponding energy surface is shown in FIG. 5. The lowest energy corresponds to the tetragonal structures associated with four equivalent minima (only three are visible in FIG. 5). The cubic structure has the highest energy (excess of about 70 meV per unit cell). The obvious candidate for a transition state between tetragonal structures with the opposite polarization is an orthorhombic structure positioned at the saddle point connecting two adjacent tetragonal valleys. The energy for the orthorhombic structure is only 20 meV above the tetragonal one.

The plotted energy surface is consistent with the ab initio work of Hong and Vanderbilt [6] where the excess energies of 45 and 11 meV per unit cell were reported for the cubic and orthorhombic structures, respectively. The discrepancy can be possibly attributed to the choice of the basis set: plane waves and pseudopotentials vs. linearized augmented plane waves (full potential) used in the present example.

Before proceeding with a discussion of external electric field effects, it will be useful to parametrize the energy surface in terms of the Landau-Devonshire phenomenology, as described in the section below.

II. Landau-Devonshire Parametrization

The free energy density of a ferroelectric crystal as a function of polarization P can be expressed as [7]

$$U_{LD}(P) = \alpha P^2 + \beta P^4 + \gamma(P_x^2 P_y^2 + P_y^2 P_z^2 + P_x^2 P_z^2), \quad (2)$$

where the energy for the parental cubic structure is taken as a reference. Here the energy expansion is limited to the fourth power in P, which is sufficient for description of the second-order phase transition [8].

The model parameters in Eq. (2) are not fully phenomenological, but can rather be related to material characteristics by $$\alpha = \frac{2U_b}{P_s^2}, \beta = \frac{U_b}{P_s^4}, \gamma = \frac{4U_b}{P_s^4}\left(\frac{U_b}{U_b^*} - 1\right). \quad (3)$$

The coefficients $\alpha$ and $\beta$ are expressed in terms of the T$\Rightarrow$C energy barrier height $U_b$ and to the spontaneous polarization for the tetragonal phase $P_s$ as previously established by Beckman et al. [9]. The coefficient $\gamma$ plays an important role in the present example, since it is responsible for the directional anisotropy of the energy surface, which is parametrized with only one additional factor $-U_b^*$ being the O$\Rightarrow$C energy barrier height.

In order to enable further analysis of external electric field effects, the energy surface presented on FIG. 5 needs to be re-cast in a polarization representation. With this purpose the polarization is calculated using the Berry phase approach [10] for individual structures that span our region of interest in the $\xi$-space (details are given in Example 1). Results for fitting of the ab initio energy surface to the free energy functional given by Eq. (2) are presented in FIG. 10. The best fit corresponds to the following set of parameters: $\alpha=600$ MV/m, $\beta=480$ MJ m C$^{-2}$ and $\gamma=640$ MJ m C$^{-2}$.

III. Anisotropy of Polarization Switching

The effect of an external electric field E on the energy profile can be taken into account by adding an electrostatic potential energy. Then the resultant energy functional (electric enthalpy) takes the form [6, 11]:

$$H(E,P) \approx U(P) - E \cdot P. \quad (4)$$

Here U(P) represents the free energy for a system in a particular polarization state that can be determined either from first principles or using the Landau-Devonshire parametrization. An effect of the external electric field on the free energy is neglected. This approach can be justified in the case of ferroelectrics, where the polarization and its response to the electric field is strongly dominated by ionic contribution in the frequency range of f~<100 MHz [12].

In order not to restrict the results to a particular choice of material parameters, it is convenient to define dimensionless quantities:

$$\mathcal{P} = \frac{P}{P_s}, \mathcal{E} = \frac{EP_s}{U_b}, \mathcal{H} = \frac{H}{U_b}. \quad (4a)$$

associated with the reduced polarization, electric field and energy density, respectively. The results shown in FIGS. 11A-C, 12, 13, 15A-D, and 16A-F are plotted in terms of these dimensionless quantities.

(A) Uniaxial Electric Field

Figure 11:
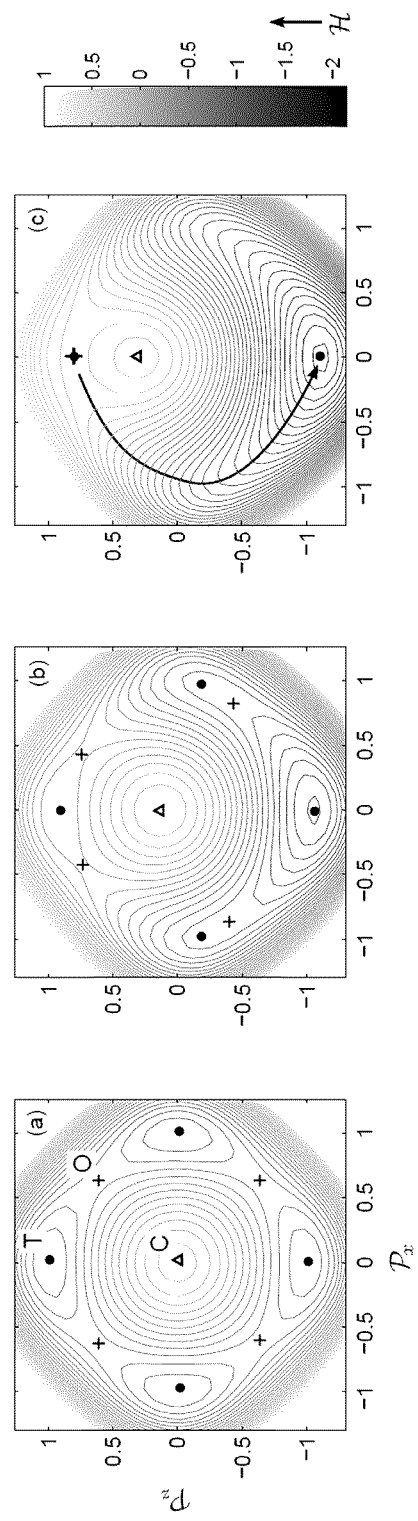
FIGS. 11A-C show the calculated schematic energy surface modified by a uniaxial external electric field $E_z$ of varying magnitude: (A) $E_z=0$, (B) $E_z=-0.5\ U_b/P_s$ and (C) $E_z=-1.1\ U_b/P_s$. Changes in the position of stationary points (minima (•), maxima (Δ) and saddle points (+)) are caused by the external field. The arrow on panel (C) illustrates the polarization rotation. The labels C, T and O refer to cubic, tetragonal and orthorhombic structures, respectively.

It is assumed that the external electric field points along [001] crystallographic direction, i.e. $E_x=E_y=0$. The field breaks the original four fold symmetry of the energy surface, shown in FIG. 11A. As the field increases, the stationary points (T, O and C) displace from their zero-field positions as shown in FIG. 11B. Such an evolution represents a modification of the equilibrium structural parameters caused by the external electric field, which is the essence of piezoelectric effect. The switching takes place when the energy of tetragonal structure merges with that for the orthorhombic structure (FIG. 11C).

In the following derivation of the coercive electric field for ferroelectric switching, the Landau-Devonshire parametrization Eq. (2) for the free energy will be used in order to keep the results general. The position of stationary points correspond to zero gradient of the enthalpy surface $$\frac{\partial U_{LD}(P)}{\partial P_z} = E_z, \quad (5a)$$

$$\frac{\partial U_{LD}(P)}{\partial P_x} = E_x, \quad (5b)$$

This set of equations has generally 9 sets of solutions $\{P_x(E_x, E_z), P_z(E_x, E_z)\}$ as show in FIG. 11B. The condition for switching by polarization rotation is:

$$P_x^{(T)} = P_x^{(O)} \text{ and } P_z^{(T)} = P_z^{(O)}. \quad (6)$$

With the assumption of $E_x=0$, equations (5) and (6) yield the following result for the coercive field in terms of the model parameters:

$$E_{c,rot} = 2\gamma\left(\frac{\alpha}{2\beta+\gamma}\right)^{3/2} = 8k(1+2k)^{-3/2}\frac{U_b}{P_s} \quad (7)$$

where $k=(U_b/U_b^*-1)$ is a coefficient that appears in Eq. (3) and characterizes the degree of anisotropy of the free energy surface. This result indicates that the coercive field is largely determined by the energy surface anisotropy and vanishes for an isotropic energy surface ($\gamma=0$ or $k=0$) as shown in FIG. 12 (solid line).

Figure 12:
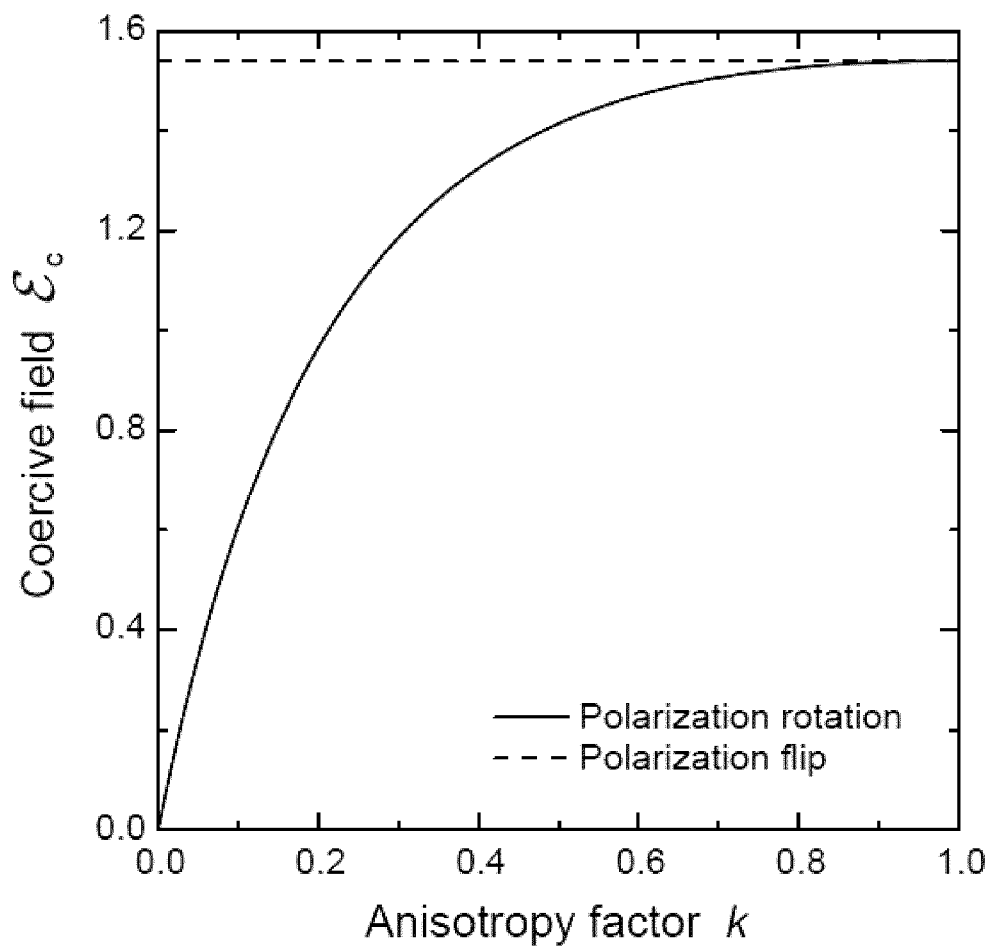
FIG. 12 is a graph illustrating the reduction of the coercive field for ferroelectric switching via polarization rotation as a function of the anisotropy factor. Uniaxial electric field is assumed (Ex=0).
Figure 13:
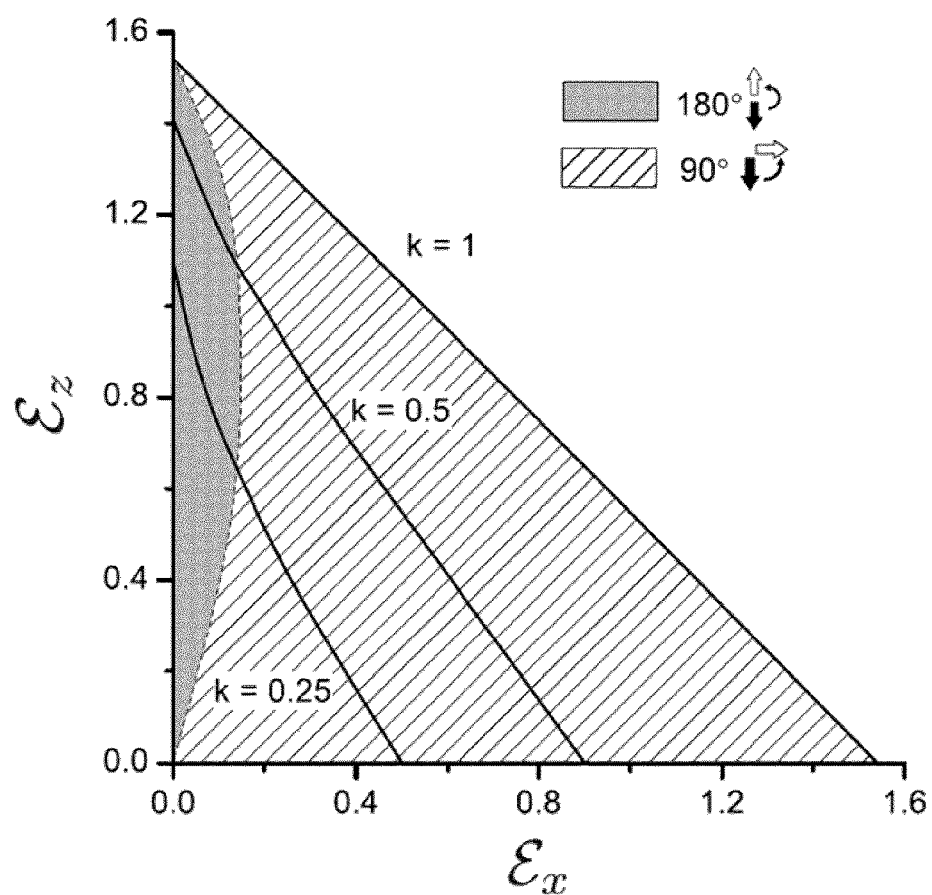
FIG. 13 plots the coercive field for ferroelectric switching via polarization rotation in response to a biaxial external electric field as a function of the anisotropy factor k. The shaded regions distinguish between areas with the full polarization inversion (180° rotation) and partial switching (90° rotation).

The coercivity approaches its maximum at $\gamma=4\beta$ ($k=1$ in FIG. 12). In this limit, the coercive field is recovered for polarization flip through the cubic structure obtained earlier by Beckman et al. [9]:

$$E_{c,fl} = (2\alpha/3)^{3/2} \beta^{-1/2} = \frac{8}{3^{3/2}} \frac{U_b}{P_S}. \quad (8)$$

The following condition needs to be fulfilled for polarization rotation to remain an energetically favourable mechanism for ferroelectric switching:

$$\frac{U_b}{U_b^*} < 2. \quad (9)$$

This result implies that the switching via orthorhombic state is favourable when the corresponding barrier is lower at least by a factor of two in comparison to the barrier for polarization flip via the cubic structure.

The energy surface of $PbTiO_3$ calculated here has the ratio $U_b/U_b^* \approx 1.4$ that clearly favours the polarization rotation. In spite of the fact that the energy barrier for the polarization switching via orthorhombic structure is as low as one third of a corresponding value for the cubic structure, the coercive field is reduced by only 14% in comparison to the switching by polarization flip (compare data in FIG. 12 at $k=0.4$). Such a high resistance to ferroelectric switching can be attributed to the absence of a tangential component of the external electric field $E_x$ to the curved switching path (FIG. 11C).

(B) Biaxial Electric Field

The in present section, the effect of additional tangential component of the electric field is investigated, particularly whether or not this additional component can facilitate the ferroelectric switching. The coercive field for an arbitrary direction E can obtained by solving the set of Eqs. (5) numerically. The results are presented in FIG. 12 for three distinct values of the anisotropy parameter k.

The coercive field has the highest magnitude when aligned with the direction of spontaneous polarization (z), which is analogous to a "hard" axis in ferromagnets. The field is greatly reduced when its direction deviates from this axis. The reduction is more pronounced in materials with a lower anisotropy of the energy surface. Here two types of switching are distinguished: 180° and 90°. The former corresponds to a complete polarization inversion, whereas the latter represents switching between two states with the mutually orthogonal polarization (an intermediate state shown in FIG. 8). The relevant switching mechanism is identified with a background shading in FIG. 13. Apparently, the polarization inversion is observed only in a narrow range of fields near to the hard axis.

Figure 14:
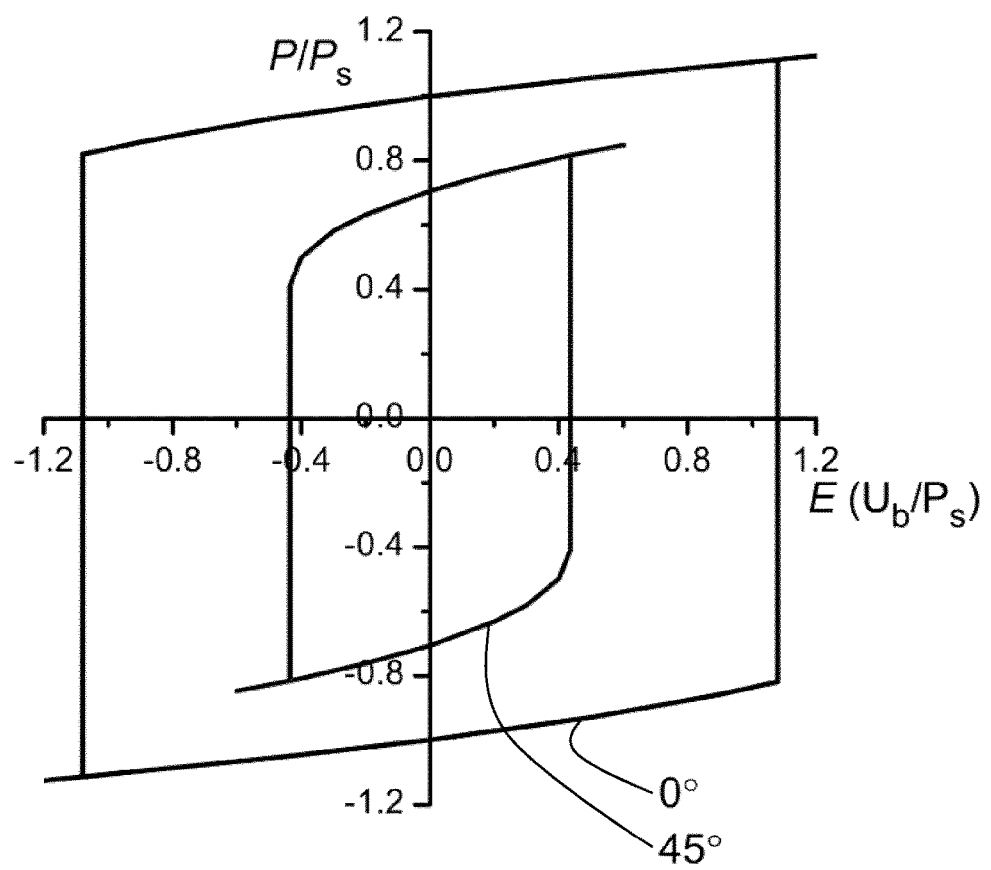
FIG. 14 presents two hysteresis curves calculated for an energy surface with k=0.25 with the external field applied along the hard (0°) and easy (45°) axis. The ferroelectric switching along the easy axis exhibits lower coercivity, but also smaller change in the polarization and, consequently, a lower mechanical response.

Since the coercive field is highly anisotropic, it is anticipated that the ferroelectric hysteresis will also be sensitive to the direction of applied electric field. FIG. 14 presents two hysteresis curves calculated for an energy surface with $k=0.25$ with the external field applied along the hard (0°) and easy (45°) axis. The ferroelectric switching along the easy axis exhibits lower coercivity, but also smaller change in the polarization and, consequently, a lower mechanical response.

IV. Polarization Switching with an Electric Field Having a Time-Dependent Orientation The preceding mathematical analysis has illustrated that the addition of a tangential field component (e.g. a non-parallel additional field component) can be useful in reducing the coercive field, albeit by a small amount. However, as noted above, and as described with reference to FIGS. 6 and 7A-B, the present inventors have found that the coercive field can be substantially reduced by using an electric field that has a time-dependent orientation, such that the central ion is driven through an intermediate path that does not pass through the central potential energy maxima.

The forthcoming section provides two non-limiting examples of driving configurations in which the electric field rotates during a switching cycle in order to substantially reduce the coercive field required for achieving polarization inversion.

Figure 15:
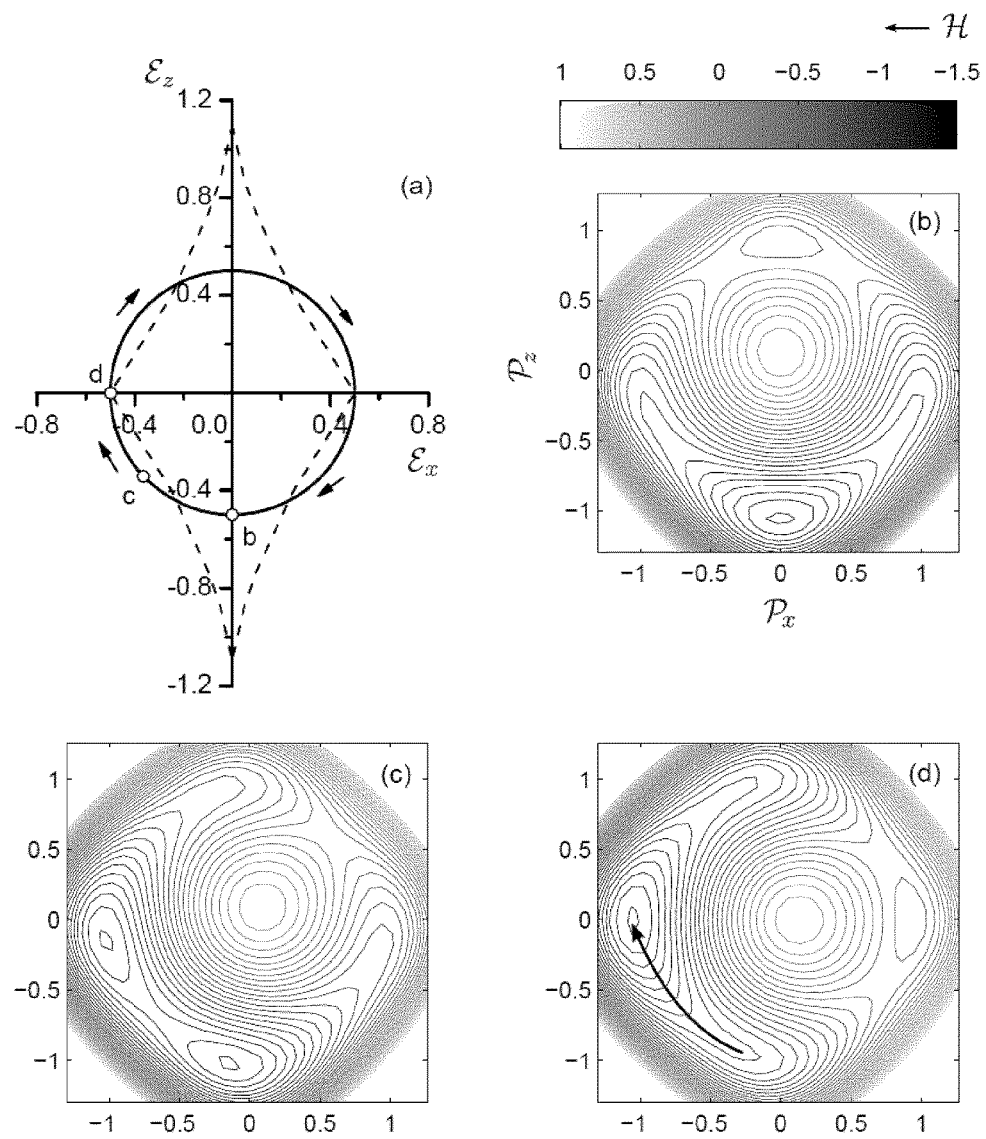
FIGS. 15A-D demonstrate 90° ferroelectric switching driven by a circularly rotating electric field (A). The excitation profile is illustrated in (A). Individual panels (B)-(D) represent the energy surface for particular excitation states with individual components of the electric field labelled on the panel (A). Since the direction of electric field deviates from the hard axis, the switching occurs at a lower field (D). The anisotropy factor k=0.25 is used for generating the energy surface. The energy density is presented in dimensionless units ($H/U_b$).
Figure 16:
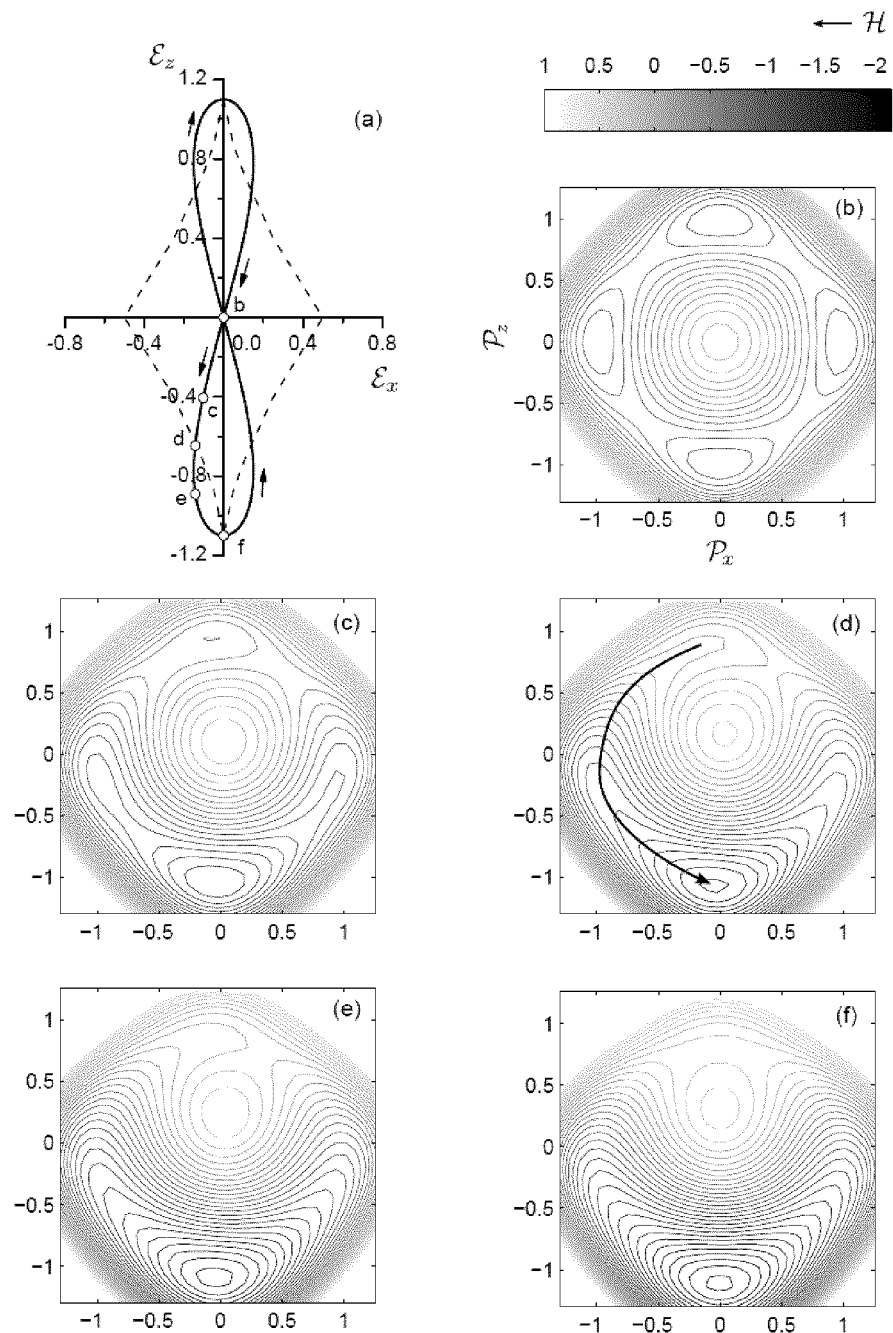
FIGS. 16A-F demonstrates 180° ferroelectric switching driven by a polar, lemniscate-like rotating electric field. The excitation profile is illustrated in (A). Individual panels (B)-(F) represent the energy surface for particular excitation states with individual components of the electric field labelled on the panel (A). Since the direction of electric field deviates from the hard axis, the switching occurs at a lower field (D). The anisotropy factor k=0.25 is used for generating the energy surface. The energy density is presented in dimensionless units ($H/U_b$).

In one non-limiting example implementation, low-coercivity polarization inversion switching is achieved when the polarization inversion is driven by a circularly rotating electric field, as illustrated in FIGS. 7A, 7B and FIGS. 15A-D. In such an example embodiment, a tangential component of the rotating electric field causes the polarization inversion via a series of successive 90° switching steps. FIG. 15A plots the evolution of the electric field during a switching cycle, and FIGS. 15B-D show the potential energy surfaces corresponding to specific points in time during the switching cycle. The anisotropy factor $k=0.25$ is used for generating the energy surfaces and the energy density is presented in dimensionless units ($H/U_b$). The coercive field, obtained from FIG. 13 for the case of $k=0.25$, is plotted in a dashed line. The Figures demonstrate only one single 90° switch based on the rotation of the electric field through one quarter of a full rotation. As shown in the Figure, the intermediate states achieved during switching in the present embodiment may correspond to the orthorhombic crystal phase.

The present example embodiment involving circular rotation of the electric field excites both longitudinal and lateral modes of excitation in an alternating fashion, which results in the alternating mechanical response in two dimensions. This may have the consequence that a substantial portion of the energy that is used for polarization inversion is coupled into undesirable excitations that may, for example, degrade the intended performance of a piezoelectric device. As such, the overall performance, and the energy efficiency, may suffer in such an embodiment if it is preferable to channel the mechanical motion into a given mode (i.e. a mode associated with the "hard" axis).

Accordingly, in other embodiments, the voltages may be applied to the ferroelectric perovskite oxide crystal such that the time-dependent electric field orientation does not correspond to a circular rotation. In particular, in some embodiments, the excitation voltages may be configured such that both the magnitude and phase of the voltages are varied during the switching cycle in order to predominantly produce excitation that is associated within a selected axis, thereby achieving polarization inversion with reduced coercivity relative to purely uniaxial excitation, while at the same time generating a desired mechanical response associated with the selected axis (e.g. mechanical excitation of a mode associated with the selected axis). For example, in some embodiments, reduced coercivity may be achieved while increasing or maximizing a mechanical response by employing a two-dimensional (or, for example, three-dimensional) electrical excitation that is preferentially oriented towards the hard axis, and results in direct polarization inversion within passing through an intermediate state.

In one example implementation of a method for producing a preferential mechanical response without switching through an intermediate state, a time-varying field E(t) is applied that takes a shape of the polar curve, such that the lemniscate-like parametric curve shown in FIGS. 16A-F. Again, the anisotropy factor k=0.25 is used for generating the energy surfaces and the energy density is presented in dimensionless units ($H/U_b$). The coercive field, obtained from FIG. 13 for the case of k=0.25, is again plotted in a dashed line. The coercive field that is achieved in this case occurs (see the intersection between the dashed line and the electric field line) within the darker gray area of FIG. 13. The advantage of such a two-dimensional excitation is that the switching takes place at a lower field (point d in FIG. 16A), while the maximum longitudinal mechanical response is expected at f-point (see FIGS. 16A-F).

Figure 17:
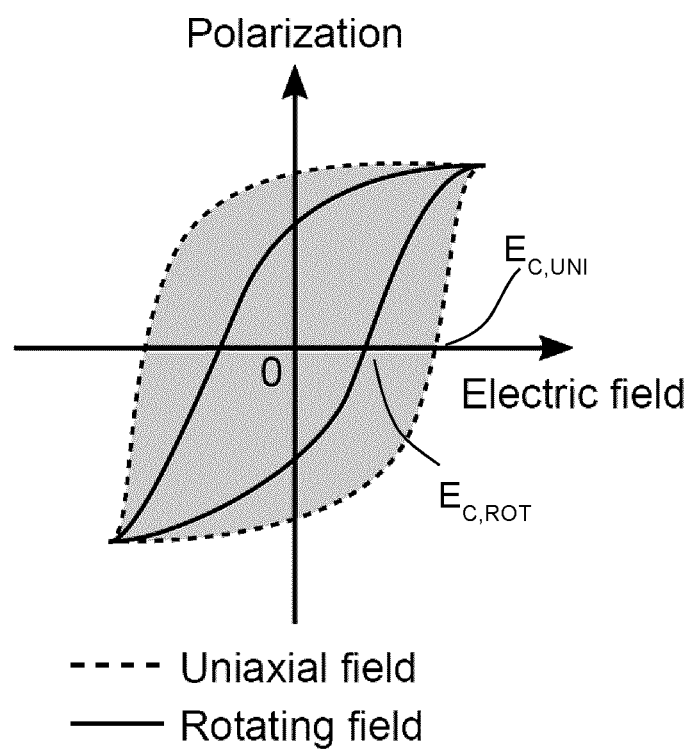
FIG. 17 illustrates the expected change in the hysteresis curve for uniaxial excitation and rotating field excitation of a ferroelectric perovskite oxide material.

FIG. 17 illustrates the expected change in the hysteresis curve for uniaxial excitation and rotating field excitation. A uniaxial excitation refers to the traditional method and the rotating field corresponds to one example implementation of the methods described herein (e.g. the lemniscate-like parametric curve shown in FIGS. 16A-F). The hysteresis loss per cycle is determined by the area of the hysteresis loop (gray area on the figure). As shown in the Figure, the coercive field achieved with the rotating electric field $E_{C,ROT}$ is less than that of the uniaxial field $E_{C,UNI}$. This reduction is expected to lead to a lower loss, thereby, for example, reducing the occurrence or probability of thermal runaway for high-power actuators. Since the quality factor is inversely proportional to the loss, it is expected that a stronger resonance amplitude of vibrational displacements may occur. The latter determines the amount of mechanical energy, which can be transmitted into the surrounding medium (e.g., water).

In another example embodiment, the rotation may be elliptical in nature, such that, for example, the major axis of the ellipse is oriented approximately along the hard axis of the ferroelectric material. This may be achieved, for example, by applying voltages having unequal magnitudes and a fixed phase delay between orthogonal pairs of electrodes. The ellipse may be selected such that the portion of the ellipse exceeding the coercive field line (the dashed line in FIG. 15A and FIG. 15A resides within the dark gray area of FIG. 13, such that the polarization inversion occurs directly without passing through an intermediate state.

It will be understood that the example driving configurations described above are not intended to be limiting, and that the electrodes may be driven according to other voltage configurations in order to achieve polarization inversion switching with less power consumption and less coercivity than conventional driving methods. For example, in other example implementations, the voltages applied to the electrodes may be controlled in order to vary any one or more of the following: the amplitude of the electric field in a first direction (e.g. $E_x$(max)), the amplitude of the electric field in a second orthogonal direction (e.g. $E_z$(max)), the ratio of the electric field amplitudes in orthogonal directions (e.g. $E_x$(max)/$E_z$(max), the phase delay between electric field components, and the ratio of the frequencies of orthogonal electric field components (e.g. $f_x/f_z$).

The preceding example methods of driving a ferroelectric material to achieve polarization inversion may be performed using an electrode configuration in which pairs of electrodes are applied or otherwise affixed to orthogonal sides of a ferroelectric material, as shown in FIG. 7A. However, it is to be understood that an electric field with a time-varying (e.g. rotating) direction may be achieved via any number of suitable electrode configurations, which may generally involve three or more additional electrodes.

The aforementioned methods may be employed for the driving of ferroelectric materials in a wide range of devices and applications. For example, the methods disclosed herein may be employed to reduce the electrical power consumption of ferroelectric devices while maintaining the magnitude of the output mechanical energy. Among the expected benefits is a reduction of the power consumption relative to uniaxial excitation. For example, in some embodiments, the power consumption may be reduced by a factor of up to approximately two. This drop in power consumption is accompanied by a corresponding reduction of the dielectric loss (undesired internal heating of the piezoelectric element). This aspect and potential benefit may have broad impact in devices and applications that employ piezoelectric materials. Example benefits that may be realized include the ability to develop smaller, more efficient devices less prone to overheating, and will reduce the power requirements in the electronics for the driving of transducers.

The amount of reduction in the coercive field will depend on the specific properties of a given ferroelectric materials. For example, in the case of PZT, it is believed that the anisotropy of the energy surface in PZT is low. For example, although direct measurements or calculations of the anisotropy do not appear to be available at present, it is known that the energy profile flattens near to the morphotropic phase boundary. An estimate of the reduction in the coercive field can be made assuming that the anisotropy factor k is approximately equal to 0.25 (k=0 and k=1 would correspond to extreme limits of highly isotropic and anisotropic energy surface, respectively). Using the excitation technique shown in FIG. 17, it would be expected that the coercive field could be lowered by approximately 30-40%, which translates to the corresponding approximately 30-40% lower hysteresis area and also lower hysteresis loss. Ideally, one would expect approximately 30-40% greater quality factor. However, it is noted that commercial PZT ceramics are random, sintered polycrystals with a variety of crystallographic orientations present in a bulk sample. Therefore, not all grains will be perfectly oriented in order to respond to the applied field as the model predicts. In order to account for such imperfection one may reduce the expected effect by a factor of approximately two.

For example, the present methods may be employed for driving ferroelectric materials for high-power applications. Examples of such high-power applications include therapeutic and imaging ultrasound, ultrasonic cleaning, plastic welding, metal surface finishing, and sonar. In some embodiments, high power may refer a power per material surface (surface power density) that is greater than approximately 0.5 W/cm$^2$ when excited in continuous mode.

High power actuators such as medical devices for therapy and ultrasonic motors dissipate a considerable amount of energy in heat. This heat dissipation limits the maximal power that can be applied on the device without introducing some adverse effect in the efficiency and stability of the device operation. By example, medical devices for therapy are often tuned to operate optimally at a single frequency, and if too much heat is present, a dilation effect can de-tune the device and then reduce the efficiency. Also, these devices are often pre-polarized, if the temperature reaches above the Curie limit, the device becomes de-polarized and becomes unusable for the intended application.

Accordingly, in some embodiments, the aforementioned methods may be employed to achieve a reduction in the heat produced when driving an ultrasonic transducer. The resulting reduction in overheating may translate into more stable operation and may allow ultrasonic devices to treat regions of human body that were unattainable because the power requirements.

For example, ultrasonic devices driven according to methods provided herein may be employed for treatment of uterine fibroids, which requires considerable power levels (>200 W at 1.2 MHz for several minutes) to treat efficiently the deepest regions of the disease.

One example of such an ultrasonic device is a small transducer that may be employed for therapy (e.g. intraurethral), or a multi-element device where each element is smaller than approximately 10 mm$^2$ (for example, such as arrays that may be used for constrained areas, such as intraoesophageal, transcranial or intracavity treatments). Such transducers will typically require approximately 1 W per element or more. Unfortunately, the elements are typically too small to withstand such power levels without overheating. In order to use such devices, efforts must be made by reducing the amount of heating. Currently, a reduction in heating can be achieved through cooling or operation in short periods of time, which can increase the treatment time or can render the treatment ineffective. Generally, such devices are operated in frequencies ranging from approximately 100 kHz to 15 MHz, although such devices may also be operated outside of this range in some applications and implementations. The power density of such devices is typically in the range of approximately 0.5 W/cm$^2$ to 5 W/cm$^2$ (the power density depends on the size of the applicator). As noted above, the methods described herein may enable the driving of such devices, for example, within this power range, while producing less heating that using conventional driving methods, and potentially avoiding problems associated with overheating, while obtaining increased mechanical energy per input driving energy (for example, potentially up to double the mechanical energy).

The present methods may be useful for compact devices or high-density arrays where mechanical limitations reduce the use of efficient cooling. For example, in some high-density devices, several hundreds of transducers can be packed within a few square centimeters, and each device is provided with its own power line. In other examples, the size of the transducer elements can range from approximately 1 mm$^2$ to 100 mm$^2$. Such constraints result in difficulty in keeping the device sufficiently cool to sustain stable operation. In addition to the aforementioned problems associated with overheating, the compact environment for high density devices also makes it possible that high temperatures can cause de-soldering issues at the electrodes connected to the transducers.

Examples of medical applications that may employ such compact/high density devices include, but are not limited to, the treatment of superficial bone metastasis, endorectal devices for the treatment of prostate cancer and colorectal cancer, catheter-based devices for a venous access for the treatment of localized diseases in the liver or the heart, tranesophageal devices for the treatment of atrial diseases in the heart or esophageal cancer, etc. It is to be understood that the preceding example applications are merely examples, and that a wide variety of therapeutic devices based on ferroelectric materials may benefit from a reduction of the heat dissipation and improvement in the energy efficiency required to operate the device.

In addition to the aforementioned high-power applications, it will be understood that embodiments of the present disclosure may be employed in low-power applications, such as applications in which the power employed to drive a piezoelectric element is less than approximately 0.5 W/cm$^2$ or that exceed that power but are excited in a pulse (burst or not continuous) mode.

It is noted that the mathematical models provided herein relate to single domain switching in the absence of mechanical constraints, which may not accurately correspond to the conditions associated with various practical implementations. For example, the majority of technologically relevant ferroelectrics are random, sintered polycrystals with a variety of crystallographic orientations present in a bulk sample [13]. Individual grains behave as a single domain when their size does not exceed approximately 150 nm [14]; larger grains exhibit a multidomain structure. Atomic scale simulations [15] show that an evolution of the polarization vector across the domain boundary resembles the polarization rotation discussed above. Among various domain structures (see, e.g., Ref. [16] and references therein), 90° zig-zag domain configuration is often reported in experimental studies [17-20]. This observation can be attributed to the low coercivity of 90° polarization rotation (FIG. 13) combined with a markedly lower formation energy of 90° domain boundaries evaluated by Meyer and Vanderbilt [15].

The following examples are presented to enable those skilled in the art to understand and to practice embodiments of the present disclosure. They should not be considered as a limitation on the scope of the disclosure, but merely as being illustrative and representative thereof.

EXAMPLES

Example 1: Details of Mathematical Model

The first-principle calculations were carried out using the density functional theory and a linear augmented plane wave basis set implemented in WIEN2K package [21]. The local spin density approximation [22] has been chosen for the exchange correlation functional. The Brillouin zone was sampled using 6×6×6 k-mesh. The radii RMT of muffin tin spheres centered at individual atoms were chosen to be equal 2.26, 1.68 and 1.49 Bohr for Pb, Ti and O, respectively. The product of the minimum RMT radius and the maximum cut-off wave vector in the reciprocal space was kept at the constant value of $R_{MT}K_{max}$=7 throughout all calculations. The energy to separate core and valence electron was set such that electrons in the following orbitals were treated as valence electrons: Pb—4f 5p 5d 6s 6p, Ti—3s 3p 3d 4s and O—2s 2p.

The fully optimized self-consistent structural parameters for PbTiO3 were used in the calculations (FIG. 9). The internal degrees of freedom for the tetragonal structure of PbTiO$_3$ were fully relaxed by minimizing the Hellmann-Feynman forces acting on atoms below 0.2 mRy/Bohr.

Polarization properties were calculated based on the modern theory of polarization [15] in the framework of Berry phase approach [23]. This capability is implemented in a BerryPI package [24] for WIEN2k used in conjunction with a WIEN2WANNIER package [25].

Example 2: Experimental Study of Dual-Mode Driving of High-Intensity Ultrasound Transducers In this example, experiments were performed to characterize the pressure and acoustic power response of a high intensity ultrasound device driven according to the methods described above. The example method employed in the present example involved simultaneously applying two sets of driving electrical signals to electrodes placed perpendicular to each other for a ring-shaped ultrasound transducer. It is shown that when both modes are driven at different constructive phases, an improvement in the driven acoustic energy can be achieved.

Sample Preparation

Figure 18A:
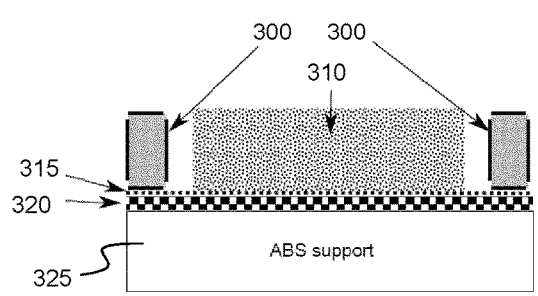
FIGS. 18A-D illustrates the format of transducer preparation and driving configuration.
Figure 18B:
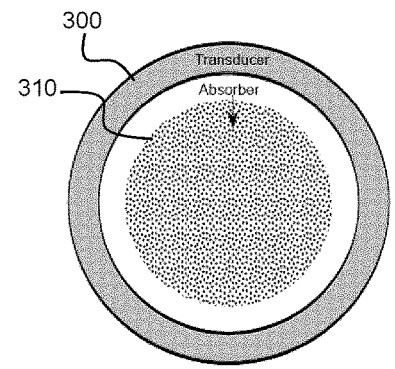

Four transducer samples were characterized. Each transducer was made of typical material for HIFU devices (DL47, Del Piezo Specialities, West Palm Beach, Fla.) and has a ring configuration as shown in FIGS. 18A and 18B. The diameter of the transducer 300 is 12 mm, with a ring width of 2 mm with a height of 4 mm. Natural resonant frequency of transducers was specified to be close as possible to 500 kHz. Transducers were configured as air-backed using a cork layer 320 below the "bottom" face of the ring transducer 300. A 0.05 mm-thick plastic film 315 was used to isolate the cork from the transducer. The ensemble was secured on a 3D-printed ABS support 325 using epoxy glue (301, epoxy technology, Billerica, Mass.).

Figure 18C:
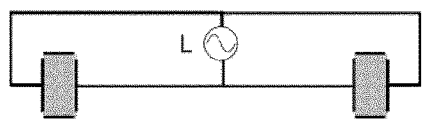
Figure 18D:

As shown in 18A and 18B, an absorber 310 made with rubber material was optionally placed at center of the opening to eliminate effects of acoustic waves travelling from and to the internal face of the ring. As noted below, measurements were performed with and without this absorber to establish the effect of this cavity in the output acoustic power. As shown in FIGS. 18C and D, two pairs of electrodes were placed following the propagation (P) mode and the lateral (L) mode. Each pair was driven independently by its own power supply. The P mode electrodes were placed on top and bottom of the ring and the L mode electrodes in the outer and inner walls of the ring. The P mode is the most common arrangement to place electrodes for high intensity applications. Each mode was electrically characterized using a network analyzer and matching circuits were build using solenoids and capacitors to adapt each mode to 50Ω.

Acoustic Measurements

Each transducer was characterized using a tank filled with degassed water with 1 ppm of oxygen. The acoustic pressure generated by the transducer was captured with a 1-mm needle hydrophone (S/N 1422, Precision Acoustics, Dorchester, Dorset, UK) mounted on a computer-controlled robotic arm (UMS2, Precision Acoustics, Dorchester, Dorset, UK). The hydrophone signal was amplified and recorded with an oscilloscope. The hydrophone was positioned at 1 cm from the top face of the transducer. The P and L modes electrodes were driven using a dual-channel function generator with 20 cycles bursts and 1 kHz repetition rate for a duty cycle of 4%. A limitation of the available equipment was that the hydrophone was not calibrated to operate in the range close to 500 kHz. Results are presented in non-dimensional units.

Pressure Vs. Phase

Figure 19A:
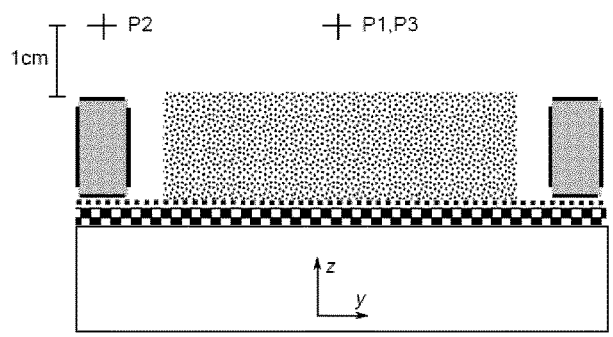
FIGS. 19A and B show the locations of points (P1, P2 and P3) where pressure vs. phase measurements were performed using a 1-mm needle hydrophone. All points were located on a plane 1-cm far away from transducer top surface. Point P1 was located at center of acoustic axis and points P2 and P3 were located directly over the transducer surface.
Figure 19B:
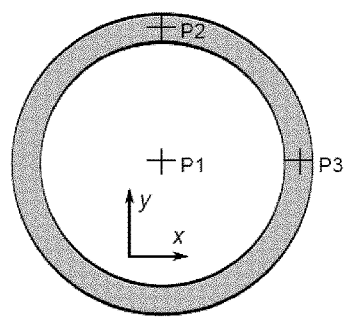
Figure 23A:
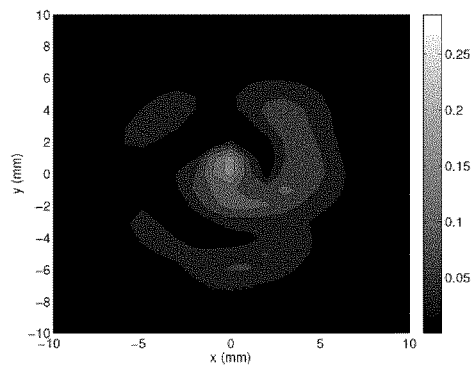
FIGS. 23A-D plot the measured acoustic intensity plans from transducer #4 perpendicular at acoustic axis located at 1 cm from the transducer surface. Data is shown when driving transducer at average frequency.
Figure 23B:
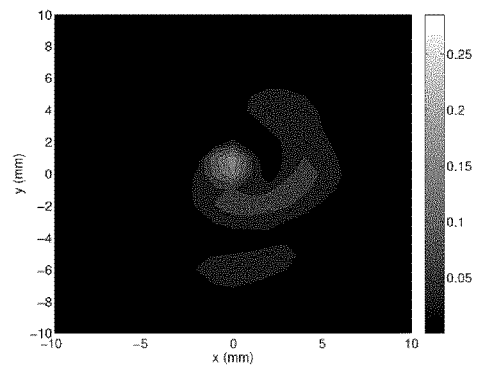
Figure 23C:
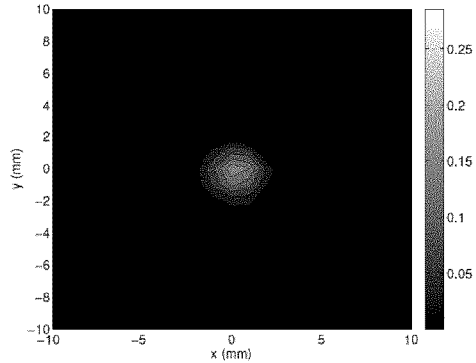
Figure 23D:
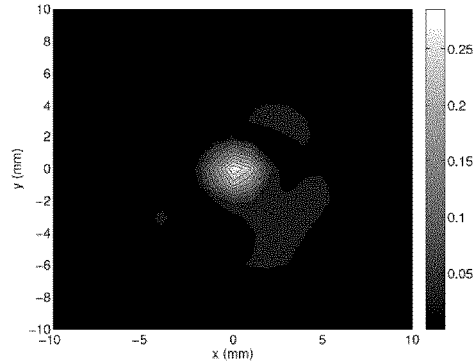

As shown in FIGS. 19A and 19B, acoustic pressure measurements were performed at the following three (3) locations: one at center of acoustic axis (P1) and two (P2, P3) directly over the top face of the ring. At each location, a series of acquisitions was done where the phase of the L mode was changed in steps of 2° (about 0.01 π-rad). In total 181 acquisitions were performed at each location to change the phase of L mode signal from 0 to 360° (0 to 2π-rad). Each series of acquisitions was repeated three times. The oscilloscope was configured to capture the whole 20-cycle burst. Data was captured with a laptop computer running Matlab R2009. Each captured signal was filtered using a low-pass analog filter (BLP-1.9+, mini circuits, Brooklyn, N.Y.) with a cut frequency of 1.9 MHz and a low-pass, zero-phase FIR digital filter using function filtfilt (Signal Processing Toolbox, Mathworks, Natick, Mass.) with a cut frequency of 1 MHz. The RMS value of the pressure signal was calculated in the central 10 cycles of the burst to ensure steady conditions.

Signal amplitudes for P and L modes were configured using a power meter to deliver 0.25 electrical W in continuous mode in each of P and L electrodes for a total of 0.5 electrical W. To measure the gain of efficiency of the P+L configuration, a series of acquisitions was performed driving only the P electrodes calibrated to send 0.5 W electrical W in continuous mode. To achieve 0.5 W for the P mode alone, the signal was amplified. Using this configuration, the P+L driving mode can be compared to the P mode alone at the same electrical power conditions.

Relative Gain in Acoustic Power at Optimal Conditions

From the pressure vs. phase data obtained in the previous section, the optimal phase was chosen with the average of the optimal phase at 3 measured locations. The relative gain in acoustic power was calculated by scanning the acoustic field in a plan of 20 mm×20 mm perpendicular to the acoustic axis. This field is large enough to capture the sound generated by the 12-mm diameter ring. The spatial step for the scanning was 1 mm, which is less than the wavelength of 500 kHz (3 mm). This ensured that the pressure at each spatial step could be considered constant over a cross-section of 1 mm². Driving and acquisitions conditions were similar as for the previous subsection. The non-dimensional acoustic power PAC was then calculated with:

$$P_{AC} = \Sigma_x \Sigma_y p_{rms}(x,y)^2,$$

where $p_{rms}(x, y)$ is the RMS value of the measured pressure at location (x, y). The relative gain was calculated by the ratio of PAC obtained using the P+L configuration at the optimal phase over the value of PAC obtained using only the P mode. As for the experiment pressure vs. phase, the total electrical power in both driving conditions remained the same with 0.5 electrical W.

To establish the effect of the cavity at the center of the ring transducer, a global set of experiments (pressure vs. phase and scanning plans) was performed with the absorber present and then a second global set without the absorber.

Results

FIG. 20 shows a table presenting the electrical characterization of each transducer. All transducers showed an effective transmitted power higher than 96%. The average resonant frequency for the P and L modes, was, respectively 461 and 460 kHz. Because the resonant frequency of both modes for each transducer was not exactly the same, experiments were conducted either driving each mode at its independent resonant frequency or driving both modes at their average frequency. This average frequency was calculated per transducer basis.

FIGS. 21A-F show the plot of the non-dimensional pressure vs. phase for transducer 4 with the absorber in place. The graph show plots of driving conditions using each resonant frequency in each mode and driving using the average frequency. FIGS. 22A-F show a similar plot for same transducer, but with the absorber removed. Both figures show clearly an effect of the phase on the L mode on the measured pressure at three different locations. However, the gain of amplitude was considerably higher when the absorber was in place. For this transducer, and with the absorber in place, a maximum of the pressure amplitude was found around 1.3π rad. The pressure was higher for points 2 and 3, but not for central point 1.

FIGS. 23A-D show the acoustic intensity plans captured for the P+L configuration with (FIG. 23A) and without (FIG. 23B) the absorber, and for the P configuration with (FIG. 23C) and without (FIG. 23D) the absorber. The power is then obtained by integrating the value of the intensity over the total area. With the absorber, the P+L configuration shows more points at high intensity over the area; and as a result higher power after integration over this area. Without the absorber, the central point of the acoustic plan shows a more intense maximum when driving only the P configuration, but after integration the total energy crossing the plan is lower when compared with P+L configuration and the absorber in place.

FIGS. 24A-F show the consolidated results for all experiments of the performance of the P+L configuration over the use of only the P mode. The figures show: adimensional power, gain in power, and optimal phase, where FIGS. 24A-C correspond to cases where the transducers are driver at their respective resonant frequencies, and FIGS. 24D-F correspond to cases where the transducers are driven at the average frequency of both modes. In this figure, the effect of the absorber is shown more evidently across all devices. All experiments combined, the P+L configuration with an absorber placed at center of the ring transducer showed the higher acoustic power output.

When compared to the P mode and with the absorber in place, an average gain (±s.d.) of 18(±12)% was observed when driving the transducer with the average frequency of both modes. When driving the transducer at the resonant frequency of each mode, this average gain reduced slightly to 12(±11)%. This observation suggests that optimal driving conditions require that both modes have to be driven with the same frequency. When compared to the P mode without the absorber, and driving with the average frequency, this gain is 64%. All experiments combined, it is worth noting that the P+L configuration showed only higher acoustic power when the absorber was in place. The absorber had also a positive effect when driving with only the P mode.

For achieving the optimal phase on the signal driving the L electrodes in the P+L configuration, it is interesting to note that results were more consistent (with less deviation) when driving the transducer at their average frequency of P and L modes. Under these conditions and the absorber in place, the average optimal phase was 1.2(±0.1) t rad. When using the resonant frequency of each mode, this average was 1.3 (±0.16) t rad.

CONCLUSIONS

The data presented in this example appears to confirm the hypothesis that a more efficient transformation of electrical power to acoustic power can be achieved when driving a piezoelectric crystal in dual driving mode, by means of connecting two pair of electrodes orthogonal one to each other, and by driving them with signals out of phase and at the same frequency. The higher acoustic power was obtained driving the transducer with the P+L configuration and including an absorber at the center of the ring transducer.

When driving the transducer (using either P+L or P configurations), a part of the energy is being transferred laterally inside the ring cavity and, potentially, creates a destructive interference. This is clearly shown by the results of the P mode driving in FIGS. 23B and D, which shows clearly larger area of high acoustic intensity when the absorber is in place, and therefore a higher power. This situation may be linked to specific conditions, such as, for example, the transducer diameter and the tested frequencies, but this observation requires that this aspect has to be considered when driving ring transducers using the P+L configuration.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

[1] Cohen, R. E. (1992). Origin of ferroelectricity in perovskite oxides. Nature; Smith, R. C., Seelecke, S., Ounaies, Z., & Smith, J. "A free energy model for hysteresis in ferroelectric materials" Journal of Intelligent Material Systems and Structures, 14(11), 719-739, 2003; Premi Chandra and Peter B. Littlewood. "A landau primer for ferroelectrics" In Physics of Ferroelectrics, volume 105 of Topics in Applied Physics, pages 69-116. Springer Berlin Heidelberg, 2007; S. P. Beckman, Xinjie Wang, Karin M. Rabe, and David Vanderbilt "Ideal barriers to polarization reversal and domain-wall motion in strained ferroelectric thin films" Phys. Rev. B, 79:144124, 2009.

[2] S. Zhang "Piezoelectric materials for high power, high temperature applications" Materials Letters 3471 (2005); M. Islam, "Real time temperature measurement for multilayered piezoelectric stack actuators" IEEE Proceedings of 24 Canadian Conference on Electrical and Computer Engineering (CCECE), 2011 pp. 001194-001197 (doi: 10.1109/CCECE.2011.6030651).

[3] Schwarz, K., & Blaha, P. (2003). Solid state calculations using WIEN2k. Computational Materials Science, 28(2), 259-273.

[4] "BerryPI: A software for studying polarization of crystalline solids with WIEN2k density functional all-electron package" by S. J. Ahmed, J. Kivinen, B. Zaporzan, L. Curiel, S. Pichardo, O. Rubel, Computer Physics Communications 647 (2013).

[6] J. Hong and D. Vanderbilt, Phys. Rev. B 84, 115107 (2011).

[7] A. Devonshire, Philos. Mag. 40, 1040 (1949).

[8] W. Cao, Ferroelectrics 375, 28 (2008).

[9] S. P. Beckman, X. Wang, K. M. Rabe, and D. Vanderbilt, Phys. Rev. B 79, 144124 (2009).

[10] R. D. King-Smith and D. Vanderbilt, Phys. Rev. B 47, 1651 (1993).

[11] R. W. Nunes and D. Vanderbilt, Phys. Rev. Lett. 73, 712 (1994).

[12] Z. Jiwei, Y. Xi, W. Mingzhong, and Z. Liangying, J. Phys. D: Appl. Phys. 34, 1413 (2001).

[13] J. E. Huber and N. A. Fleck, J. Mech. Phys. Solids 49, 785 (2001).

[14] S. Ren, C. Lu, J. Liu, H. Shen, and Y. Wang, Phys. Rev. B 54, R14337 (1996).

[15] B. Meyer and D. Vanderbilt, Phys. Rev. B 65, 104111 (2002).

[16] C.-C. Chou and C.-S. Chen, Ceram. Int. 26, 693 (2000).

[17] W. J. Merz, Phys. Rev. 95, 690 (1954).

[18] G. Arlt, D. Hennings, et al., J. Appl. Phys. 58, 1619 (1985).

[19] C.-C. Chou, C.-S. Hou, and T.-H. Yeh, J. Eur. Ceram. Soc. 25, 2505 (2005).

[20] G. Catalan, A. Schilling, J. F. Scott, and J. M. Gregg, J. Phys.: Condens. Matter 19, 132201 (2007).

[21] P. Blaha, K. Schwarz, G. K. H. Madsen, D. Kvasnicka, and J. Luitz, Wien2k: An Augmented Plane Wave+Local Orbitals Program for Calculating Crystal Properties (Karlheinz Schwarz, Techn. Universitat Wien, Austria, 2001).
[22] J. P. Perdew and Y. Wang, Phys. Rev. B 45, 13244 (1992).
[23] M. V. Berry, Proc. R. Soc. London Ser. A 392, 45 (1984).
[24] S. Ahmed, J. Kivinen, B. Zaporzan, L. Curiel, S. Pichardo, and O. Rubel, Comput. Phys. Commun. 184, 647 (2013).
[25] J. Kunes, R. Arita, P. Wissgott, A. Toschi, H. Ikeda, and K. Held, Comput. Phys. Commun. 181, 1888 (2010).

Therefore what is claimed is:

1. A method of electrically driving a ferroelectric material to achieve polarization inversion, the ferroelectric material having an anisotropic potential energy surface with an energy barrier for a curved switching path that is lower than for the barrier for a direct path associated with uniaxial switching, the method comprising:
applying time-dependent voltages to the ferroelectric material in at least two directions; and
controlling the voltages such that the orientation of the electric field within the ferroelectric material varies with time during the switching cycle, such that the coercive field is reduced relative to the coercive field required for uniaxial excitation;
wherein the voltages are applied such that the coercive field is exceeded during the switching cycle, thereby achieving polarization inversion.

2. The method according to claim 1 wherein the voltages are a first voltage and a second voltage, and wherein the first voltage and the second voltage are applied in directions that are approximately orthogonal.

3. The method according to claim 1 wherein the voltages are applied such that the electric field rotates within the ferroelectric material during the switching cycle.

4. The method according to claim 3 wherein the voltages are applied such that the electric field rotates in a circular orientation with an approximately constant magnitude.

5. The method according to claim 4 wherein the voltages are applied such that the ferroelectric material switches to an intermediate orthorhombic phase prior to achieving polarization inversion.

6. The method according to claim 3 wherein the rotation of the electric field is elliptical.

7. The method according to claim 6 wherein the major axis of the elliptical rotation is oriented approximately along the hard axis of the ferroelectric material.

8. The method according to claim 1 wherein the voltages are applied such that the electric field rotates in a polar configuration.

9. The method according to claim 8 wherein the polar configuration is a lemniscate-like parametric curve.

10. The method according to claim 1 wherein the voltages are configured such that both the magnitude and phase of the voltages are varied during the switching cycle in order to predominantly produce excitation that is associated within a selected axis, thereby achieving polarization inversion with reduced coercivity relative to purely uniaxial excitation, while generating a desired mechanical response associated with the selected axis.

11. The method according to claim 1 wherein the voltages controlled to vary one or more of the amplitude of the electric field in a first direction, the amplitude of the electric field in a second direction, the ratio of the electric field amplitudes in orthogonal directions, the phase delay between electric field components, and the ratio of the frequencies of orthogonal electric field components.

12. The method according to claim 1 wherein the ferroelectric material comprises a ferroelectric perovskite oxide crystal.

13. The method according to claim 1 wherein the ferroelectric material is selected from the group consisting of PZT, $PbTiO_3$, $BaTiO_3$, and $LiNbO_3$.

14. The method according to claim 1 wherein the applied surface power density exceeds approximately 0.5 $W/cm^2$.

15. The method according to claim 1 wherein the ferroelectric material is polycrystalline.

16. The method according to claim 1 wherein the ferroelectric material is a single crystal.

17. The method according to claim 1 wherein the ferroelectric material is a component of a therapeutic ultrasonic device.

18. A method of electrically driving an ultrasonic device, the ultrasonic device comprising one or more ferroelectric elements having an anisotropic potential energy surface with an energy barrier for a curved switching path that is lower than for the barrier for a direct path associated with uniaxial switching, the method comprising:
applying time-dependent voltages to the one or more ferroelectric elements in at least two directions; and
controlling the voltages such that the orientation of the electric field within the one or more ferroelectric elements varies with time during the switching cycle, such that the coercive field is reduced relative to the coercive field required for uniaxial excitation;
wherein the voltages are applied such that the coercive field is exceeded during the switching cycle, thereby achieving polarization inversion.

19. The method according to claim 18 wherein the one or more ferroelectric elements are provided in an array.

20. An ultrasonic device comprising:
one or more ferroelectric elements, each ferroelectric element having an anisotropic potential energy surface with an energy barrier for a curved switching path that is lower than for the barrier for a direct path associated with uniaxial switching; and
control circuitry connected to the ferroelectric elements for applying time-dependent voltages to the one or more ferroelectric elements in at least two directions;
wherein the voltages are provided by the control circuitry such that the orientation of the electric field within the one or more ferroelectric elements varies with time during the switching cycle, such that the coercive field is reduced relative to the coercive field required for uniaxial excitation; and
wherein the voltages are provided by the control circuitry such that the coercive field is exceeded during the switching cycle, thereby achieving polarization inversion.

* * * * *